(12) United States Patent
Yilmaz et al.

(10) Patent No.: US 9,670,415 B2
(45) Date of Patent: Jun. 6, 2017

(54) SYNTHESIS OF ZEOLITIC MATERIALS USING N,N-DIMETHYL ORGANOTEMPLATES

(75) Inventors: Bilge Yilmaz, New York, NY (US); Ulrich Berens, Binzen (DE); Vijay Narayanan Swaminathan, Mumbai (IN); Ulrich Müller, Neustadt (DE); Gabriele Iffland, Heidelberg (DE); Laszlo Szarvas, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 1167 days.

(21) Appl. No.: 13/605,701

(22) Filed: Sep. 6, 2012

(65) Prior Publication Data
US 2013/0059723 A1 Mar. 7, 2013

Related U.S. Application Data

(60) Provisional application No. 61/531,102, filed on Sep. 6, 2011.

(51) Int. Cl.
*C01B 39/54* (2006.01)
*C01B 39/48* (2006.01)
(Continued)

(52) U.S. Cl.
CPC .............. *C10G 3/49* (2013.01); *B01J 29/70* (2013.01); *B01J 29/7015* (2013.01);
(Continued)

(58) Field of Classification Search
CPC ......... C01B 39/04; C01B 39/48; C01B 39/54; B01J 29/7015; B01J 29/85
See application file for complete search history.

(56) References Cited

U.S. PATENT DOCUMENTS 3,459,676 A * 8/1969 Kerr ................ C01B 39/48
423/705
4,499,327 A * 2/1985 Kaiser ................ B01J 29/85
423/305
(Continued)

FOREIGN PATENT DOCUMENTS

CN 101489648 7/2009
JP 2009-541040 A 11/2009
(Continued)

OTHER PUBLICATIONS

"International Search Report and Written Opinion of PCT/IB2012/054596", mailed on Jan. 24, 2013, 13 pgs.
(Continued)

*Primary Examiner* — David M Brunsman
(74) *Attorney, Agent, or Firm* — Oblon, McClelland, Maier & Neustadt, L.L.P.

(57) ABSTRACT

The present invention relates to a process for the preparation of a zeolitic material having a structure comprising $YO_2$ and optionally comprising $X_2O_3$, preferably comprising $YO_2$ and $X_2O_3$, wherein said process comprises the steps of (1) providing a mixture comprising one or more ammonium compounds of which the ammonium cation has the formula (I):

$$[R^1R^2NR^3R^4]^+ \qquad (I)$$

and further comprising one or more sources for $YO_2$ and one or more sources for $X_2O_3$;

(2) crystallizing the mixture provided in (1);

wherein Y is a tetravalent element, and X is a trivalent element, and wherein in formula (I)

$R^1$ and $R^2$ are independently from one another derivatized or underivatized methyl, and (Continued)

$R^3$ and $R^4$ are independently from one another derivatized or underivatized ($C_3$-$C_5$)alkyl, and
wherein the molar ratio of ammonium cation having the formula (I) to Y in the mixture provided in step (1) and crystallized in step (2) is equal to or greater than 0.25.

21 Claims, 4 Drawing Sheets

(51) Int. Cl.
| | | |
|---|---|---|
| *B01J 29/70* | (2006.01) | |
| *B01J 29/85* | (2006.01) | |
| *B01J 29/86* | (2006.01) | |
| *B01J 29/87* | (2006.01) | |
| *C10G 3/00* | (2006.01) | |
| *C10G 11/05* | (2006.01) | |
| *C07C 1/20* | (2006.01) | |
| *C10G 25/03* | (2006.01) | |
| *C10G 11/18* | (2006.01) | |
| *B01D 53/94* | (2006.01) | |

(52) U.S. Cl.
CPC ............ *C01B 39/48* (2013.01); *C01B 39/54* (2013.01); *C07C 1/20* (2013.01); *C10G 11/05* (2013.01); *C10G 11/18* (2013.01); *C10G 25/03* (2013.01); *B01D 53/9413* (2013.01); *B01D 53/9436* (2013.01); *B01D 2255/50* (2013.01); *B01J 29/85* (2013.01); *B01J 29/86* (2013.01); *B01J 29/87* (2013.01); *B01J 2229/183* (2013.01); *C07C 2529/70* (2013.01); *C10G 2300/405* (2013.01); *Y02C 20/10* (2013.01)

(56) References Cited

U.S. PATENT DOCUMENTS

| | | | | |
|---|---|---|---|---|
| 4,544,538 A | * | 10/1985 | Zones | ..................... B01J 29/70 423/706 |
| 7,094,389 B2 | * | 8/2006 | Cao | ........................ C01B 37/02 423/706 |
| 7,754,187 B2 | * | 7/2010 | Cao | ........................ B01J 29/80 423/703 |
| 8,715,618 B2 | * | 5/2014 | Trukhan | ............. B01D 53/9418 423/703 |
| 2007/0244341 A1 | | 10/2007 | Kremer et al. | |
| 2007/0244391 A1 | * | 10/2007 | Hirota | ................... A61B 5/0066 600/443 |
| 2008/0045767 A1 | | 2/2008 | Cao et al. | |
| 2009/0196812 A1 | | 8/2009 | Bull et al. | |
| 2011/0196183 A1 | | 8/2011 | Nesterenko et al. | |
| 2012/0244066 A1 | * | 9/2012 | Bull | ................... B01D 53/9418 423/703 |

FOREIGN PATENT DOCUMENTS

| | | |
|---|---|---|
| JP | 2009-541040 A5 | 11/2009 |
| JP | 2011-510899 A | 4/2011 |
| WO | WO-2008/000380 | 1/2008 |
| WO | WO 2010/023289 A1 | 3/2010 |

OTHER PUBLICATIONS

Xu, Hong et al., "Synthesis and properties of a zeolite LEV analogue from the system—Na2O—Al2O3—SiO2—N,N-dimethylpiperidine chloride-H2O", *Catalysis Today* 148 2006 , pp. 6-11.

Burwell, Robert L. , "Definitions, Terminology and Symbols in Colloid and Surface Chemistry, Part II: Heterogeneous Catalysis", *Terminology for Physicochemical Quantities and Units—Appendix II* Pure & Appl. Chem, vol. 46 1976 , pp. 71-90.

Campbell, Branton J. et al., "The Synthesis of the New Zeolite, ERS-7, and the Determination of its Structure by Simulated Annealing and Synchrotron X-ray Powder Diffraction", *Chem. Commun.* 1998 , pp. 1725-1726.

Xie, Bin et al., "Seed-directed Synthesis of Zeolites With Enhanced Performance in the Absence of Organic Templates", *Chem. Comm.*, vol. 47 2011 , pp. 3945-3947.

Japanese Office Action issued Jul. 12, 2016 in Patent Application No. 2014-527806 (with English language translation).

* cited by examiner

SYNTHESIS OF ZEOLITIC MATERIALS USING N,N-DIMETHYL ORGANOTEMPLATES

CROSS-REFERENCE TO RELATED APPLICATIONS

This application claims priority under 35 U.S.C. §119(e) to U.S. Provisional Application No. 61/531,102, filed Sep. 6, 2011, the entire disclosure of which is incorporated by reference herein.

TECHNICAL FIELD

Embodiments of the invention relate to processes for the production of zeolitic materials as well as to zeolitic materials which may be obtained from such a process. Furthermore, embodiments of the invention relate to the use of zeolitic materials as may be obtained from such a process.

INTRODUCTION

Molecular sieves are classified by the Structure Commission of the International Zeolite Association according to the rules of the IUPAC Commission on Zeolite Nomenclature. According to this classification, framework-type zeolites and other crystalline microporous molecular sieves, for which a structure has been established, are assigned a three letter code and are described in the Atlas of Zeolite Framework Types, 5th edition, Elsevier, London, England (2001). Chabazite and Levyne are well studied examples of zeolitic materials, wherein Chabazite is the classical representative of the class of zeolitic materials having a CHA framework structure, and Levyne for its part is the classical representative of the class of zeolitic materials having an LEV framework structure. Both compounds and related materials having the given framework structure are employed in a variety of applications, and in particular serve as heterogeneous catalysts in a wide range of reactions such as in methanol to olefin catalysis and selective catalytic reduction of nitrogen oxides $NO_x$ to name some two of the most important applications. Zeolitic materials of both the CHA and LEV framework type are three-dimensional 8-membered-ring (8MR) pore/channel systems containing double-six-rings (D6R) and cages. The difference between the two structures stems from the stacking of the double-six-rings and cages.

Synthetic Chabazite and CHA-type zeolites are synthesized with the help of structure-directing agents, typically using exotic organotemplates such as adamantyl ammonium-based compounds. Same applies with respect to synthetic Levyne and LEV-type zeolites which are typically also prepared using exotic structure-directing agents such as quinuclidine-based organotemplates. Although recently lower-cost organotemplates such as diethyldiemethyl ammonium hydroxide have been discovered for the synthesis of LEV-type zeolites, this is yet not the case for the synthesis of Chabazite and related materials having the CHA-type framework. The problem therefore remains, in particular with respect to the synthesis of Chabazite and related materials having the CHA-type framework structure, that cost-intensive organotemplate materials must be employed in procedures for their preparation.

Furthermore, said problem is accentuated by the fact that the cost-intensive materials employed as structure-directing agents are trapped in the zeolitic materials obtained from template synthesis. As such, their removal is necessary in order to open the porous volume of the materials for the actual utilization, e.g. as molecular sieves or in catalysis. Complete removal of the structure-directing agents, however, is difficult and is normally only achieved by calcination at high temperatures, a procedure which greatly increases the production costs since the organic template is destroyed in the process and may therefore not be recycled.

Campbell et al., Chem. Commun. 1998, 16, 1725-1726 disclose the use of N,N-dimethylpiperidinium as a structure directing agent in the synthesis of zeolitic materials having the MOR, MTW, LEV, and NON-type framework structure, in addition to the zeolite ERS-7.

As an alternative to said methods, organotemplate-free synthetic methodologies have been developed which rely on the seeding of synthesis mixtures in the absence of structure-directing agents. Xie et al., Chem. Commun. 2011, 47, 3945-3947 for example discloses seed-directed syntheses of zeolite Beta, Levyne, and Heulandite zeolites in the absence of organotemplates. Although such methods afford a solution to problems encountered in preparation methods involving the use of organotemplates, in particular in view of production costs and environmental issues related to the waste products generated during the removal of the organotemplates, such seeded syntheses are limited to very few types of zeolites. In particular, organotemplate-free synthetic methodologies are not available for the production of Chabazite and other zeolitic materials having a CHA-type framework structure.

Furthermore, seeded syntheses afford very specific crystallization products. In the particular case of crystallization products having more than one type of framework element in the oxide structure such as e.g. in aluminosilicates including both Si and Al as framework elements in the oxides, the distribution of Si and Al is clearly different to the distribution found in zeolitic materials obtained from organotemplate mediated syntheses. Accordingly, particular features such as e.g. specific catalytic activities found for zeolitic materials obtained from synthetic methodologies may not be reproduced in the products obtained from organotemplate-free synthetic methodologies due to said differences in composition and structure, and in particular due to the different distribution of framework elements in the crystallized products.

Accordingly, there is a need for novel synthetic methodologies involving the use of organotemplates which may afford new zeolitic materials which may not be obtained with the aid of organotemplate-free synthetic methodologies. Furthermore, there remains a need for finding new organotemplates which do not involve high production costs. Finally, there is an ongoing need for finding new synthetic methodologies involving the use of organotemplates which may afford new zeolitic materials having new and interesting properties, in particular with respect to the numerous applications in which zeolites find widespread use, such as in the field of molecular sieves and as versatile catalysts for use in a variety of chemical conversions.

SUMMARY

One or more embodiments of the invention are directed to processes for the preparation of zeolitic materials having a structure comprising $YO_2$ and optionally comprising $X_2O_3$, preferably comprising $YO_2$ and $X_2O_3$, wherein said process comprises the steps of (1) providing a mixture comprising one or more ammonium compounds of which the ammonium cation has the formula (I):

$$[R^1R^2NR^3R^4]^+ \quad (I)$$

and further comprising one or more sources for $YO_2$ and one or more sources for $X_2O_3$;
(2) crystallizing the mixture provided in (1);
wherein Y is a tetravalent element, and X is a trivalent element, and wherein in formula (I) $R^1$ and $R^2$ are independently from one another derivatized or underivatized, preferably underivatized methyl, and $R^3$ and $R^4$ are independently from one another derivatized or underivatized, preferably underivatized ($C_3$-$C_5$)alkyl, preferably $C_3$ or $C_4$ alkyl, wherein more preferably $R^3$ and $R^4$ form a common ($C_4$-$C_8$)alkyl chain, more preferably a common ($C_4$-$C_7$)alkyl chain, more preferably a common ($C_4$-$C_6$)alkyl chain, wherein more preferably said common alkyl chain is a derivatized or underivatized, preferably underivatized $C_4$ or $C_5$ alkyl chain, even more preferably a derivatized or underivatized, preferably underivatized $C_5$ alkyl chain, and wherein the molar ratio of ammonium cation having the formula (I) to Y in the mixture provided in step (1) and crystallized in step (2) is equal to or greater than 0.25, wherein said molar ratio is preferably comprised in the range of from 0.25 to 5, more preferably of from 0.25 to 3, more preferably of from 0.25 to 2, more preferably of from 0.3 to 1.7, more preferably of from 0.4 to 1.5, more preferably of from 0.45 to 1.3, more preferably of from 0.5 to 1.2, and even more preferably of from 0.55 to 1.15.

In some embodiments, the one or more ammonium compounds provided in step (1) comprises one or more ammonium compounds selected from the group consisting of derivatized or underivatized, preferably underivatized N,N-dimethylpyrrolidinium compounds, N,N-dimethylpiperidinium compounds, N,N-dimethylhexahydroazepinium compounds, and mixtures of two or more thereof, preferably one or more compounds selected from the group consisting of derivatized or underivatized, preferably underivatized N,N-dimethylpyrrolidinium compounds, N,N-dimethylpiperidinium compounds, and mixtures of two or more thereof, wherein even more preferably the ammonium compound comprises one or more derivatized or underivatized, preferably underivatized N,N-dimethylpiperidinium compounds.

In one or more embodiments, Y is selected from the group consisting of Si, Sn, Ti, Zr, Ge, and mixtures of two or more thereof, wherein Y preferably comprises Si, and wherein even more preferably Y is Si.

In some embodiments, the one or more sources for $YO_2$ comprises one or more compounds selected from the group consisting of silicas, silicates, and mixtures of two or more thereof, wherein preferably the one or more sources for $YO_2$ comprise one or more silicas, wherein more preferably the one or more sources for $YO_2$ comprise fumed silica, and wherein even more preferably the source for $YO_2$ is fumed silica.

In one or more embodiments, X is selected from the group consisting of Al, B, In, Ga, and mixtures of two or more thereof, wherein X preferably comprises Al, B, or Ga, wherein more preferably X comprises Al and/or B, and wherein even more preferably X is Al or B.

In some embodiments, the one or more sources for $X_2O_3$ comprises one or more compounds selected from the group consisting of aluminas, aluminates, and mixtures of two or more thereof, wherein preferably the one or more sources for $X_2O_3$ comprises one or more aluminates, preferably one or more alkali metal aluminates, more preferably one or more alkali metal aluminates comprising sodium and/or potassium aluminate, preferably sodium aluminate, wherein even more preferably the source for $X_2O_3$ is sodium and/or potassium aluminate, and preferably sodium aluminate.

In one or more embodiments, the structure of the zeolitic material further comprises $Z_2O_5$ in addition to $YO_2$ and $X_2O_3$, and wherein the mixture provided in step (1) further comprises one or more sources for $Z_2O_5$, wherein Z is a pentavalent element.

In some embodiments, Z is selected from the group consisting of P, As, Sb, Bi, V, Nb, Ta, and mixtures of two or more thereof, preferably from the group consisting of P, As, V, and mixtures of two or more thereof, wherein more preferably Z comprises P or As, preferably P, and wherein even more preferably Z is P.

In one or more embodiments, the $YO_2$:$X_2O_3$ molar ratio of the mixture provided in step (1) ranges from 1 to 400 or greater, preferably from 5 to 300, more preferably from 10 to 200, more preferably from 20 to 150, more preferably from 40 to 120, and even more preferably from 50 to 100.

In some embodiments, the mixture provided in step (1) further comprises a solvent, wherein said solvent preferably comprises water, more preferably distilled water, wherein even more preferably the solvent is water, preferably distilled water. In detailed embodiments, the $H_2O$:$YO_2$ molar ratio of the mixture provided in step (1) ranges from 1 to 150, preferably from 3 to 100, more preferably from 5 to 60, more preferably from 8 to 45, more preferably from 10 to 35, more preferably from 11 to 30, and even more preferably from 12 to 28 and/or, and wherein the $H_2O$:$X_2O_3$ molar ratio of the mixture provided in step (1) ranges from 100 to 8,000, preferably from 500 to 5,000, more preferably from 1,000 to 3,600, more preferably from 1,100 to 3,000, and even more preferably from 1,150 to 2,700. In certain embodiments, the pH of the mixture provided in step (1) is comprised in the range of from 8 to 14, preferably from 10 to 14, more preferably from 11 to 14, more preferably from 12 to 14, more preferably from 13 to 14, and even more preferably from 13.6 to 13.8.

In some embodiments, the crystallization in step (2) involves heating of the mixture, preferably at a temperature ranging from 80 to 250° C., more preferably from 100 to 200° C., more preferably from 120 to 180° C., more preferably from 130 to 170° C., more preferably from 140 to 160° C., and even more preferably from 145 to 155° C. In detailed embodiments, heating in step (2) is conducted under solvothermal conditions, preferably under hydrothermal conditions. In certain embodiments, the crystallization in step (2) involves heating of the mixture for a period ranging from 0.1 to 20 d, preferably from 0.5 to 15 d, more preferably from 1 to 10 d, more preferably from 2 to 8 d, more preferably from 3 to 7 d, more preferably from 4 to 6 d, and even more preferably from 4.5 to 5.5 d.

Some embodiments of the invention further comprise one or more steps of
(3) isolating the zeolitic material, preferably by filtration, and/or
(4) washing the zeolitic material, and/or
(5) drying the zeolitic material.
Detailed embodiments further comprise one or more steps of
(6) calcining the zeolitic material obtained according to (2) or (3) or (4) or (5),
wherein the steps (3) and/or (4) and/or (5) and/or (6) can be conducted in any order, and wherein at least one of said steps is preferably repeated one or more times.

Additional embodiments of the invention are directed to synthetic zeolitic materials having a structure comprising $YO_2$ and optionally comprising $X_2O_3$, preferably comprising $YO_2$ and $X_2O_3$, said material being obtainable and/or obtained, preferably obtained, by a process according to any of the process claims.

Further embodiments of the invention are directed to synthetic zeolitic materials having a CHA framework structure, said zeolitic material being optionally obtainable and/or obtained by a process according to any of the process claims, wherein the zeolitic material comprises $YO_2$ and $X_2O_3$, wherein Y is a tetravalent element and X is a trivalent element, and wherein the zeolitic material displays a Y:X molar ratio comprised in the range of from 1 to 10.5, preferably of from 1 to 9, more preferably of from 1 to 7, more preferably of from 1 to 6, more preferably of from 1.5 to 5, more preferably of from 1.5 to 4.5, more preferably of from 2 to 4, more preferably of from 2 to 3.75, more preferably of from 2.5 to 3.75, more preferably of from 3 to 3.75, and even more preferably of from 3.25 to 3.75, wherein when the zeolitic material optionally further comprises $Z_2O_5$ in addition to $YO_2$ and $X_2O_3$, wherein Z is a pentavalent element, and wherein the zeolitic material then displays a Y:nX:pZ molar ratio, the value for the ratio (1+2p):(n−p) is then comprised in the range of from 1 to 5.5, preferably in the range of from 1.5 to 5, more preferably of from 1.5 to 4.5, more preferably of from 2 to 4, more preferably of from 2 to 3.75, more preferably of from 2.5 to 3.75, more preferably of from 3 to 3.75, and even more preferably of from 3.25 to 3.75.

In detailed embodiments, the material comprises one or more zeolites selected from the group consisting of (Ni(deta)$_2$)-UT-6, Chabazite, |Li—Na|[Al—Si—O]-CHA, DAF-5, Dehyd. Na-Chabazite, K-Chabazite (Iran), LZ-218, Linde D, Linde R, MeAPSO-47, Phi, SAPO-34, SAPO-47, SSZ-13, SSZ-62, UiO-21, Willhendersonite, ZK-14, ZYT-6, and combinations of two or more thereof.

Additional embodiments of the invention are directed to synthetic zeolitic materials having an LEV framework structure, said zeolitic material being obtainable and/or obtained by a process according to any of the process claims, wherein the zeolitic material comprises $YO_2$ and $X_2O_3$, wherein Y is a tetravalent element and X is a trivalent element, and wherein the zeolitic material displays a Y:X molar ratio comprised in the range of from 1 to 9.25, more preferably of from 2 to 9, more preferably of from 2.5 to 8.5, more preferably of from 3 to 8, more preferably of from 3.5 to 7.5, more preferably of from 4 to 7, more preferably of from 4.5 to 6.5, more preferably of from 5 to 6, and even more preferably of from 5.25 to 5.75, wherein when the zeolitic material optionally further comprises $Z_2O_5$ in addition to $YO_2$ and $X_2O_3$, wherein Z is a pentavalent element, and wherein the zeolitic material then displays a Y:nX:pZ molar ratio, the value for the ratio (1+2p):(n−p) is then comprised in the range of from 1 to 20, preferably in the range of from 1 to 15, more preferably of from 1 to 10, more preferably of from 2 to 9, more preferably of from 2.5 to 8.5, more preferably of from 3 to 8, more preferably of from 3.5 to 7.5, more preferably of from 4 to 7, more preferably of from 4.5 to 6.5, more preferably of from 5 to 6, and even more preferably of from 5.25 to 5.75.

In some embodiments, the material comprises one or more zeolites selected from the group consisting of Levyne, LZ-132, NU-3, RUB-1, ZK-20, ZSM-45, RUB-50, and mixtures of two or more thereof, wherein preferably the zeolitic material comprises RUB-50.

In one or more embodiments, Z is selected from the group consisting of P, As, Sb, Bi, V, Nb, Ta, and mixtures of two or more thereof, preferably from the group consisting of P, As, V, and mixtures of two or more thereof, wherein more preferably Z comprises P or As, preferably P, and wherein even more preferably Z is P.

In some embodiments, the framework structure does not contain a pentavalent element Z in addition to $YO_2$ and $X_2O_3$.

Further embodiments of the invention are directed to synthetic zeolitic materials having a layered structure comprising $YO_2$ and optionally comprising $X_2O_3$, wherein Y is a tetravalent element, and X is a trivalent element, said material being optionally obtainable and/or obtained by a process according to any of claims 1 to 17, wherein said material has an X-ray diffraction pattern comprising at least the following reflections:

| Diffraction angle 2 Theta/° [Cu K(alpha 1)] | Intensity (%) |
|---|---|
| 5.5-5.8 | 4-16 |
| 19.29-19.59 | 7-19 |
| 20.8-21.4 | 4-16 |
| 23.87-24.17 | 3-15 |
| 28.38-28.68 | 4-21 |
| 30.6-30.9 | 2-14 |
| 35.98-36.28 | 1-10 | wherein 100% relates to the intensity of the maximum peak in the X-ray diffraction pattern.

In some embodiments, Y is selected from the group consisting of Si, Sn, Ti, Zr, Ge, and mixtures of two or more thereof, wherein Y preferably comprises Si, and wherein even more preferably Y is Si.

In one or more embodiments, X is selected from the group consisting of Al, B, In, Ga, and mixtures of two or more thereof, wherein X preferably comprises Al or Ga, wherein more preferably X comprises Al, and wherein even more preferably X is Al.

Additional embodiments of the invention are directed to uses of zeolitic materials according to any of the claims as a molecular sieve, as an adsorbent, for ion-exchange, as a catalyst and/or as a catalyst support, preferably as a catalyst for the selective catalytic reduction (SCR) of nitrogen oxides $NO_x$; for the oxidation of $NH_3$, in particular for the oxidation of $NH_3$ slip in diesel systems; for the decomposition of $N_2O$; as an additive in fluid catalytic cracking (FCC) processes; or as a catalyst in organic conversion reactions, preferably in the conversion of alcohols to olefins, and more preferably in methanol to olefin (MTO) catalysis.

Further embodiments of the invention are directed to methods of catalyzing a reaction comprising contacting a substance with the zeolitic material of the claims, wherein the zeolitic material acts as one or more of a molecular sieve, an adsorbent, an ion-exchanger, a catalyst and a catalyst support. In detailed embodiments, the zeolitic material acts as one or more of a catalyst for the selective catalytic reduction (SCR) of nitrogen oxides $NO_x$; for the oxidation of $NH_3$, in particular for the oxidation of $NH_3$ slip in diesel systems; for the decomposition of $N_2O$; as an additive in fluid catalytic cracking (FCC) processes; or as a catalyst in organic conversion reactions, preferably in the conversion of alcohols to olefins, and more preferably in methanol to olefin (MTO) catalysis.

BRIEF DESCRIPTION OF THE DRAWINGS

The powder X-ray diffraction patterns displayed in the figures were recorded on a Bruker-AXS D8 Advance Series 2 X-ray diffractometer with monochromatic Cu K alpha-1 radiation. The diffraction data were collected using a SOL-XE energy dispersive X-ray detector. In the figures, the angle 2 Theta in ° is shown along the abscissa and the intensities are plotted along the ordinate.

DETAILED DESCRIPTION

Figure 1:
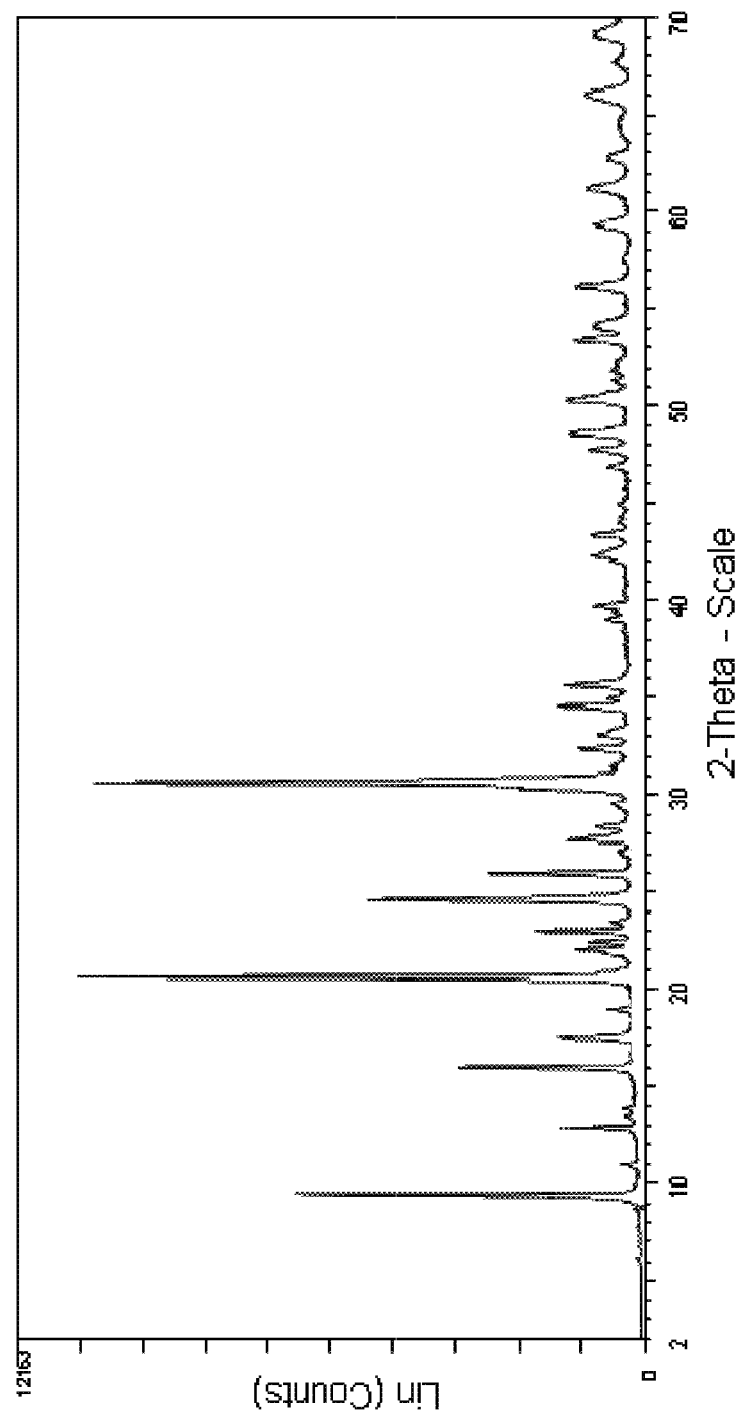
FIGS. 1 to 3 show the X-ray diffraction pattern of the crystalline material obtained in Examples 1 to 3, respectively. In each figure, the x axis shows the 2 Theta values, with tick marks, from the left, of 2, 10, 20, 30, 40, 50, 60, and 70. In each figure, the y axis shows the Lin(Counts), wherein, from bottom to top, FIG. 1 starts at 0 and ends at 12163, FIG. 2 starts at 0 and ends at 12690, and FIG. 3 starts at 0 and ends at 28361.

One or more embodiments of the invention are directed to novel synthetic methodologies for the production of novel zeolitic materials displaying unprecedented physical and chemical properties. It has unexpectedly been found that the use of N,N-dimethyl organotemplates as structure directing agents may be used to afford zeolitic materials having the CHA-type framework structure.

Furthermore, it has quite surprisingly been found that when used in specific amounts, the N,N-dimethyl organotemplate may also afford zeolitic materials of the LEV-type framework with unprecedented characteristics. For example, in the specific case of aluminosilicate structures, it has unexpectedly been found that zeolitic materials having the LEV-type framework structure may be obtained which display unprecedented Si:Al molar ratios as obtained from syntheses involving the use of organotemplates as structure directing agents. More specifically, it has quite surprisingly been found that the unique physical properties and chemical reactivities of zeolitic materials obtained from organotemplate mediated synthesis may be extended to Si:Al molar ratios which have until now not been achieved.

Finally, it has surprisingly been found that the use of N,N-dimethyl organotemplates may also afford novel zeolitic materials having a layered structure.

Thus, one or more embodiments of the present invention relate to processes for the preparation of zeolitic materials having a structure comprising $YO_2$ and optionally comprising $X_2O_3$, preferably comprising $YO_2$ and $X_2O_3$, wherein said process comprises the steps of
(1) providing a mixture comprising one or more ammonium compounds of which the ammonium cation has the formula (I):

$$[R^1R^2NR^3R^4]^+ \quad (I)$$

and further comprising one or more sources for $YO_2$ and one or more sources for $X_2O_3$;
(2) crystallizing the mixture provided in (1);
wherein Y is a tetravalent element, and X is a trivalent element, and
wherein in formula (I)
$R^1$ and $R^2$ are independently from one another derivatized or underivatized, preferably underivatized methyl, and
$R^3$ and $R^4$ are independently from one another derivatized or underivatized, preferably underivatized $(C_3-C_5)$alkyl, preferably $C_3$ or $C_4$ alkyl, wherein more preferably $R^3$ and $R^4$ form a common $(C_4-C_8)$alkyl chain, more preferably a common $(C_4-C_7)$alkyl chain, more preferably a common $(C_4-C_6)$alkyl chain, wherein more preferably said common alkyl chain is a derivatized or underivatized, preferably underivatized $C_4$ or $C_5$ alkyl chain, even more preferably a derivatized or underivatized, preferably underivatized $C_5$ alkyl chain, and
wherein the molar ratio of ammonium cation having the formula (I) to Y in the mixture provided in step (1) and crystallized in step (2) is equal to or greater than 0.25, wherein said molar ratio is preferably comprised in the range of from 0.25 to 5, more preferably of from 0.25 to 3, more preferably of from 0.25 to 2, more preferably of from 0.3 to 1.7, more preferably of from 0.4 to 1.5, more preferably of from 0.45 to 1.3, more preferably of from 0.5 to 1.2, and even more preferably of from 0.55 to 1.15.

In particular, it has quite surprisingly been found that the use of higher concentrations of N,N-dimethyl organotemplates may afford novel zeolitic materials having the CHA and LEV-type framework structures, as well as zeolitic materials having a layered structure. These findings are all the more unexpected since the presence of structure directing agents and in particular of organotemplates in reaction mixtures is generally regarded as a simple necessity for the formation of the characteristic microporous frameworks of such materials, in particular with respect to those materials which may otherwise not be obtained. More specifically, it is generally accepted that a sufficient amount shall be present in the reaction mixture for enabling the formation of the zeolitic framework around them via self-assembly processes, wherein it is desirable that they not be used in a greater amount than is absolutely necessary in view of their cost as well as due to the aforementioned environmental aspects incurred by their use.

Thus, according to some embodiments of the present invention, the amount of the one or more ammonium compounds provided in step (1) of the inventive process is chosen such, that the molar ratio of ammonium cation having the formula (I) to Y in said mixture is equal to or greater than 1:4, i.e. equal to or greater than 0.25. In this respect, it must be noted that according to the present invention there is no general restriction as to the maximal molar content of ammonium cation according to formula (I) which may be provided in the mixture according to step (1) relative to the molar content of Y contained in the one or more sources for $YO_2$ equally contained in said mixture. Thus, in principle, any suitable amount of the one or more ammonium compounds containing the ammonium cation according to formula (I) may be provided in step (1), provided that the molar ratio of said one or more ammonium cations to Y contained in the mixture of step (1) is equal to or greater than 0.25, and that a zeolitic material having a structure comprising $YO_2$ may be obtained from crystallization in step (2). By way of example, the amount of the one or more ammonium compounds provided in step (1) may be chosen such that the molar ratio of the one or more ammonium cations according to the formula (I) to Y contained in the mixture is comprised in the range of from 0.25 to 5, wherein it is preferred that said molar ratio is comprised in the range of from 0.25 to 5, more preferably of from 0.25 to 3, more preferably of from 0.25 to 2, more preferably of from 0.3 to 1.7, more preferably of from 0.4 to 1.5, more preferably of from 0.45 to 1.3, and more preferably of from 0.5 to 1.2. According to particularly preferred embodiments, the molar ratio of said one or more ammonium cations to Y contained in the mixture of step (1) is of from 0.55 to 1.15.

According to particular embodiments of the present invention, the molar ratio of said one or more ammonium cations to Y contained in the mixture of step (1) is comprised in the range of from 0.25 to 5, preferably of from 0.3 to 3, more preferably of from 0.4 to 2, more preferably of from 0.6 to 1.7, more preferably of from 0.8 to 1.4, more preferably of from 1 to 1.2, and even more preferably of from 1.1 to 1.15. Alternatively, according to further embodiments of the present invention which are preferred, the molar ratio of said one or more ammonium cations to Y contained in the mixture of step (1) is comprised in the range of from 0.25 to 3, preferably of from 0.3 to 2, more preferably of from 0.4 to 1.2, more preferably of from 0.45 to 0.9, more preferably of from 0.5 to 0.7, and even more preferably of from 0.55 to 0.6.

Accordingly, it was highly unexpected that the use of N,N-dimethyl organotemplates in unusually high amounts as in the present invention may afford completely different and novel crystallization products compared to those obtained when using such templates in lower amounts as known in the art. In particular, it has surprisingly been discovered that in the case of the N,N-dimethyl organotemplates of the present invention, beyond the effect of providing a structure directing agent allowing for the formation of the microporous characteristics of the zeolitic materials, a highly unexpected concentration effect has been discovered which allows for the formation of the novel zeolitic materials of the present invention.

Within the meaning of the present invention the term "zeolitic material" generally refers to any zeolite containing material. According to a preferred meaning, the term zeolitic material refers to one or more zeolites. "Zeolites" as related to in the context of the present invention are crystalline compounds with well-ordered channel or cage structures containing micropores. The expression "micropore" as used in the context of the present invention corresponds to the definition given in "Pure Applied Chemistry" (1976), Vol. 45, p. 71 ff., in particular p. 79. According to this definition, micropores are pores with a pore diameter of less than 2 nm. The network of these zeolites is made of $YO_4$ and $XO_4$-tetrahedra that are bridged via shared oxygen bonds. An overview of the known structures can be found in, e.g., W. M. Meier and D. H. Olson in "Atlas of Zeolite Structure Types", Elsevier, 4th Ed., London 1996. In addition to micropores, the zeolitic materials according to the invention may also contain mesopores and/or macropores as well. Furthermore, the zeolitic materials of the present invention also encompass zeolites and related materials having a layered structure. In particular, zeolitic materials having a layered structure are characterized in that in their X-ray diffraction pattern they display one or more intense reflections, preferably one intense reflection, at low diffraction angles, wherein preferably the most intense reflection has the lowest 2 Theta value among the reflections resulting from the zeolitic material having the layered structure. According to a particularly preferred meaning of the present invention, the term "zeolite" refers to one or more aluminosilicate compounds, and the term "zeolitic material" accordingly to a material containing one or more zeolites, and more preferably to the one or more zeolites themselves.

Furthermore, in the zeolitic material which may be obtained according to the inventive process, $YO_2$ and $X_2O_3$ optionally comprised therein are contained in the framework structure of the zeolitic material as structure building elements, as opposed to non-framework elements which can be present in the pores and/or cavities formed by the framework structure and typical for zeolitic materials in general.

According to embodiments of the present invention, one or more compounds having ammonium cations according to the following formula (I) are provided in the mixture according to step (1) of the inventive process:

$[R^1R^2NR^3R^4]^+$          (I)

wherein said ammonium cations act as structure directing agents for the crystallization of the zeolitic material having a structure comprising $YO_2$ and $X_2O_3$. In formula (I), $R^1$ and $R^2$ independently from one another stand for derivatized or underivatized methyl. Within the meaning of the present invention, the term "underivatized methyl" stands for the functional group —$CH_3$. The term "derivatized methyl" on the other hand stands for any conceivable chemical derivatization of the methyl group, provided that the resulting ammonium cation according to formula (I) may act as a structure-directing agent during the crystallization in step (2) of the inventive process. Thus, one or more hydrogen atoms of the methyl moiety may be chemically modified, provided that the resulting ammonium cation according to formula (I) may be used as an organotemplate for the crystallization of a zeolitic material comprising $YO_2$ and preferably comprising $YO_2$ and $X_2O_3$ in step (2) of the inventive process. In this respect, there is no particular restriction as to the number of hydrogen atoms which may be chemically modified, nor with respect to the type of chemical modification. Thus, by way of example, one to three of the hydrogen atoms of the methyl moiety, preferably one or two, and even more preferably one of the hydrogen atoms of either or both of the groups $R^1$ and $R^2$ may be substituted by one or more chemical functionalities selected from the group consisting of halogen, OH, alkoxy, $NH_2$, thiol, thioether, formyl, acyl, or a derivative thereof, preferably from the group consisting of F, Cl, Br, OH, $NH_2$, thiol, or a derivative thereof, more preferably from the group consisting of F, Cl, and Br, wherein even more preferably one or more of the three hydrogen atoms of the methyl group, preferably one or two, and even more preferably one of the hydrogen atoms is replaced by Cl and/or F, preferably by F. According to the present invention it is however particular preferred that one or both and preferably that both methyl groups $R^1$ and $R^2$ are underivatized methyl groups —$CH_3$.

Furthermore, $R^3$ and $R^4$ in formula (I) independently from one another stand for derivatized or underivatized ($C_3$-$C_5$) alkyl. Within the meaning of the present invention, "underivatized alkyl" stands for —$C_nH_{(2n+1)}$, wherein n=3-5, preferably 3 or 4. According to preferred embodiments according to which $R^3$ and $R^4$ form a common alkyl chain, the term "underivatized alkyl" stands for —$C_nH_{2n}$—, wherein n=4-8, preferably 4-7, more preferably 4-6, more preferably 4 or 5, and even more preferably 5. On the other hand, as for the term "underivatized methyl", the term "underivatized alkyl" stands for any conceivable derivatization of the alkyl group, provided that the resulting ammonium cation according to formula (I) may act as a structure-directing agent during the crystallization in step (2) of the inventive process. Thus, one or more hydrogen atoms of the alkyl moiety may be chemically modified, provided that the resulting ammonium cation according to formula (I) may be used as an organotemplate for the crystallization of a zeolitic material comprising $YO_2$ and preferably comprising $YO_2$ and $X_2O_3$ in step (2) of the inventive process. In this respect, there is no particular restriction as to the number of hydrogen atoms of the alkyl moiety which may be chemically modified, nor with respect to the type of chemical modification. Thus, by way of example, anywhere from one to seven of the hydrogen atoms of a given alkyl moiety, preferably one to five, more preferably one to three, more preferably one or two, and even more preferably one of the hydrogen atoms of either or both of the groups $R^3$ and $R^4$ may be substituted by one or more chemical functionalities selected from the group consisting of halogen, OH, alkyl, alkoxy, $NH_2$, alkylamino, dialkylamino, thiol, thioether, formyl, acyl, alkoxycarbonyl, or a derivative thereof, preferably from the group consisting of F, Cl, Br, OH, $(C_1-C_3)$ alkyl, $(C_1-C_3)$alkoxy, $NH_2$, $(C_1-C_3)$alkylamino, $di(C_1-C_3)$ alkylamino, thiol, $(C_1-C_3)$thioether, formyl, $(C_1-C_3)$acyl, $(C_1-C_3)$alkoxycarbonyl, or a derivative thereof, more preferably from the group consisting of F, Cl, Br, OH, $(C_1-C_3)$ alkyl, $(C_1-C_3)$alkoxy, or a derivative thereof, more preferably from the group consisting of F, Cl, and Br, wherein even more preferably one or more of the hydrogen atoms of the alkyl group, preferably one to five, more preferably one to three, more preferably one or two, and even more preferably one of the hydrogen atoms of a given alkyl moiety is replaced by Cl and/or F, preferably by F. According to the present invention it is however particular preferred that one or both and preferably that both methyl groups $R^3$ and $R^4$ are underivatized alkyl groups $-C_nH_{(2n+1)}$, wherein n=3-5, preferably 3 or 4. According to preferred embodiments in which $R^3$ and $R^4$ form a common alkyl chain, it is particularly preferred that said alkyl chain is an underivatized alkyl chain $-C_nH_{2n}-$, wherein n=4-8, preferably 4-7, more preferably 4-6, more preferably 4 or 5, and even more preferably 5.

According to some embodiments of the invention, the one or more ammonium compounds provided in step (1) comprises one or more ammonium compounds selected from the group consisting of derivatized or underivatized, preferably underivatized N,N-dimethylpyrrolidinium compounds, N,N-dimethylpiperidinium compounds, N,N-dimethylhexahydroazepinium compounds, and mixtures of two or more thereof. As regards the derivatized and underivatized representatives of the aforementioned groups of compounds, the same applies with respect to the individual substituents of the alkylammonium cations contained therein as applies with respect to preferred and particularly preferred embodiments of the ammonium cation of formula (I) of the present invention as outlined in the present application. Thus, with respect to the methyl groups contained in the N,N-dimethylpyrrolidinium compounds, N,N-dimethylpiperidinium compounds, and N,N-dimethylhexahydroazepinium compounds according to the present invention, these may be independently from one another derivatized or underivatized, and preferably underivatized methyl groups as defined for preferred and particularly preferred embodiments of the ammonium cation of formula (I) with respect to the groups $R^1$ and $R^2$ defined therein. Furthermore, with respect to the $C_4$-, $C_5$-, and $C_6$-alkyl chain respectively contained in the N,N-dimethylpyrrolidinium compounds, N,N-dimethylpiperidinium compounds, and N,N-dimethylhexahydroazepinium compounds, the same apply with respect to derivatized and underivatized embodiments thereof as with respect to preferred and particularly preferred embodiments of the ammonium cation of formula (I) with respect to the groups $R^3$ and $R^4$ defined therein.

According to one or more embodiments of the invention with respect to the one or more ammonium compounds provided in the mixture of step (1) the one or more ammonium compounds of some embodiments are selected from the group consisting of one or more compounds selected from the group consisting of derivatized or underivatized, preferably underivatized N,N-dimethylpiperidinium compounds, N,N-dimethylhexahydroazepinium compounds, and mixtures of two or more thereof. According to embodiments of the present invention, the one or more ammonium compounds provided in the mixture of step (1) comprise one or more derivatized or underivatized, preferably one or more underivatized N,N-dimethylpiperidinium compounds.

In some embodiments, the one or more ammonium compounds provided in step (1) comprises one or more ammonium compounds selected from the group consisting of derivatized or underivatized, preferably underivatized N,N-dimethylpyrrolidinium compounds, N,N-dimethylpiperidinium compounds, N,N-dimethylhexahydroazepinium compounds, and mixtures of two or more thereof, preferably one or more compounds selected from the group consisting of derivatized or underivatized, preferably underivatized N,N-dimethylpyrrolidinium compounds, N,N-dimethylpiperidinium compounds, and mixtures of two or more thereof, wherein even more preferably the ammonium compound comprises one or more derivatized or underivatized, preferably underivatized N,N-dimethylpiperidinium compounds.

According to the present invention, a zeolitic material is crystallized in step (2). Said material comprises $YO_2$, wherein Y stands for any conceivable tetravalent element, Y standing for either one or several tetravalent elements. Preferred tetravalent elements according to the present invention include Si, Sn, Ti, Zr, and Ge, and combinations of two or more thereof. More preferably, Y stands for Si, Ti, or Zr, or any combination of said tetravalent elements, even more preferably for Si and/or Sn. According to the present invention, it is particularly preferred that Y stands for Si.

Thus, according to preferred embodiments of the present invention, Y is selected from the group consisting of Si, Sn, Ti, Zr, Ge, and mixtures of two or more thereof, wherein Y preferably comprises Si, and wherein even more preferably Y is Si.

Furthermore, according to the process of the present invention one or more sources for $YO_2$ can be provided in step (1) in any conceivable form, provided that a zeolitic material comprising $YO_2$ can be crystallized in step (2). Preferably, $YO_2$ is provided as such and/or as a compound which comprises $YO_2$ as a chemical moiety and/or as a compound which (partly or entirely) is chemically transformed to $YO_2$ during the inventive process.

In preferred embodiments of the present invention, wherein Y stands for Si or for a combination of Si with one or more further tetravalent elements, the source for $SiO_2$ preferably provided in step (1) can be any conceivable source. There can therefore be used, for example, all types of silica and/or silicates, preferably fumed silica, silica hydrosols, reactive amorphous solid silicas, silica gel, silicic acid, water glass, sodium metasilicate hydrate, sesquisilicate or disilicate, colloidal silica, pyrogenic silica, silicic acid esters, or tetraalkoxysilanes, or mixtures of at least two of these compounds.

Among the silicates which may be employed, alkali metal silicates are preferred, more preferably water glass, more preferably sodium and/or potassium silicate, and even more preferably sodium silicate. Among the silica which may be employed, fumed silica is preferred. According to some embodiments the at least one source for $SiO_2$ comprises silica, preferably fumed silica.

Therefore, it is preferred according to the present invention that the one or more sources for $YO_2$ comprises one or more compounds selected from the group consisting of silicas, silicates, and mixtures of two or more thereof, wherein preferably the one or more sources for $YO_2$ comprise one or more silicas, wherein more preferably the one or more sources for $YO_2$ comprise fumed silica, and wherein even more preferably the source for $YO_2$ is fumed silica.

According to the present invention, the zeolitic material crystallized in step (2) optionally further comprises $X_2O_3$, wherein X stands for any conceivable trivalent element, X standing for either one or several trivalent elements. Preferred trivalent elements according to the present invention include Al, B, In, and Ga, and combinations thereof. More preferably, X stands for Al, B, or Ga, or any combination of said trivalent elements, even more preferably for Al and/or B. According to embodiments of the present invention, it is particularly preferred that X stands for Al.

Therefore, according to preferred embodiments of the present invention, X is selected from the group consisting of Al, B, In, Ga, and mixtures of two or more thereof, wherein X preferably comprises Al, B, or Ga, wherein more preferably X comprises Al and/or B, and wherein even more preferably X is Al or B.

According to the inventive process, one or more sources for $X_2O_3$ are provided in step (1). In general, $X_2O_3$ can be provided in any conceivable form, provided that a zeolitic material comprising $X_2O_3$ can be crystallized in step (2). Preferably, $X_2O_3$ is provided as such and/or as a compound which comprises $X_2O_3$ as a chemical moiety and/or as a compound which (partly or entirely) is chemically transformed to $X_2O_3$ during the inventive process.

In preferred embodiments of the present invention, wherein X stands for Al or for a combination of Al with one or more further trivalent elements, the source for $Al_2O_3$ provided in step (1) can be any conceivable source. There can be used for example any type of alumina and aluminates, aluminum salts such as, for example, alkali metal aluminates, aluminum alcoholates, such as, for example, aluminum triisopropylate, or hydrated alumina such as, for example, alumina trihydrate, or mixtures thereof. Preferably, the source for $Al_2O_3$ comprises at least one compound selected from the group consisting of alumina and aluminates, preferably aluminates, more preferably alkali metal aluminates, wherein even more preferably, the alkali metal of the aluminate comprises one or more of the alkali metals M. Among the preferred alkali metal aluminates, the at least one source preferably comprises sodium and/or potassium aluminate, more preferably sodium aluminate. In some embodiments of the present invention, the source for $Al_2O_3$ is sodium aluminate.

According to further preferred embodiments of the present invention wherein X stands for B or for a combination of B with one or more further trivalent elements, the source for $B_2O_3$ provided in step (1) can again be any conceivable source. By way of example, free boric acid and/or borates and/or boric esters may be provided as the source for $B_2O_3$, such as, for example, triethyl borate or trimethyl borate. According to the present invention it is preferred that the source for $B_2O_3$ comprises one or more boron containing compounds selected from the group consisting of free boric acid, borates, boric esters, and mixtures of two or more thereof, preferably from the group consisting of boric acid, borates, and mixtures of two or more thereof. In some embodiments of the present invention, the source for $B_2O_3$ is boric acid.

According to some embodiments of the inventive process, the mixture according to step (1) comprises at least one silica as a source for $YO_2$ and at least one aluminate as a source for $X_2O_3$, more preferably at least one fumed silica and/or at least one alkali metal aluminate, wherein the alkali metal of said preferred embodiments preferably comprises sodium and/or potassium, more preferably sodium, and wherein the alkali metal even more preferably is sodium. According to further embodiments of the present invention which are particularly preferred, the mixture according to step (1) comprises at least one silica as a source for $YO_2$ and one or more boron containing compound as a source for $X_2O_3$, more preferably at least one silica and one or more boron containing compounds selected from the group consisting of free boric acid, borates, boric esters, and mixtures of two or more thereof, wherein according to some embodiments, the mixture according to step (1) comprises fumed silica and boric acid.

Therefore, it is preferred according to the present invention that wherein the one or more sources for $X_2O_3$ comprises one or more compounds selected from the group consisting of aluminas, aluminates, and mixtures of two or more thereof, wherein preferably the one or more sources for $X_2O_3$ comprises one or more aluminates, preferably one or more alkali metal aluminates, more preferably one or more alkali metal aluminates comprising sodium and/or potassium aluminate, preferably sodium aluminate, wherein even more preferably the source for $X_2O_3$ is sodium and/or potassium aluminate, and preferably sodium aluminate. Alternatively, it is preferred that the one or more sources for $X_2O_3$ comprises one or more compounds selected from the group consisting of boric acid, borates, boric esters, and mixtures of two or more thereof, preferably from the group consisting of boric acid, borates, and mixtures of two or more thereof, wherein even more preferably the one or more sources for $X_2O_3$ comprises boric acid.

According to preferred embodiments of the present invention, the zeolitic material crystallized in step (2) further comprises $Z_2O_5$, wherein Z stands for any conceivably pentavalent element, Z standing for either one or several pentavalent elements. In said preferred zeolitic material which may be obtained according to the inventive process, $Z_2O_5$ comprised therein is contained in the framework structure of the zeolitic material as structure building element, as opposed to non-framework elements which can be present in the pores and/or cavities formed by the framework structure and typical for zeolitic materials in general. Preferred pentavalent elements Z according to the present invention include P, As, Sb, Bi, V, Nb, Ta, and mixtures of two or more thereof. More preferably, Z stands for one or more elements selected from the group consisting of P, As, V, and mixtures of two or more thereof, wherein more preferably Z comprises P or As. According to particularly preferred embodiments thereof, Z comprises P, wherein it is particularly preferred that Z is P.

Regarding preferred embodiments of the present invention wherein the zeolitic material which may be obtained according to the inventive process further includes $Z_2O_5$ in addition to $YO_2$ and optionally $X_2O_3$, preferably in addition to both $YO_2$ and $X_2O_3$, said $Z_2O_5$ is equally contained in the framework structure of the zeolitic material as structure building element, as opposed to non-framework elements which can be present in the pores and/or cavities formed by the framework structure and typical for zeolitic materials in general.

Therefore, according to preferred embodiments of the present invention, the zeolitic material further comprises $Z_2O_5$ in addition to $YO_2$ and $X_2O_3$, wherein the mixture provided in step (1) further comprises one or more sources for $Z_2O_5$, wherein Z is a pentavalent element. According to said preferred embodiments, it is particularly preferred the Z is selected from the group consisting of P, As, Sb, Bi, V, Nb, Ta, and mixtures of two or more thereof, preferably from the group consisting of P, As, V, and mixtures of two or more thereof, wherein more preferably Z comprises P or As, preferably P, and wherein even more preferably Z is P.

In preferred embodiments of the present invention wherein Z stands for P or for a combination of P with one or more further pentavalent elements, the source for $P_2O_5$ provided in step (1) can be any conceivable source. There can be used for example any type of phosphorous oxides, phosphates, acids of phosphorous, or mixtures thereof. Preferably the source for $Z_2O_5$ comprises at least one compound selected from the group consisting of phosphates, acids of phosphorous, and mixtures thereof, wherein even more preferably the one or more sources for $Z_2O_5$ provided in step (1) comprises one or more acids of phosphorous, preferably phosphoric acid. According to some embodiments of the present invention, the source for $Z_2O_5$ is phosphoric acid.

In general, according to the present invention, the $YO_2$:$X_2O_3$ molar ratio of the mixture provided in step (1) can have any conceivable value, provided that a zeolitic material comprising $YO_2$ and optionally comprising $X_2O_3$, preferably comprising $YO_2$ and $X_2O_3$, is crystallized in step (2). Generally, the molar ratio ranges anywhere from 0.5 to 300. According to the present invention it is however preferred that the $YO_2$:$X_2O_3$ molar ratio of the mixture provided in step (1) is comprised in the range of from 1 to 400 or greater, preferably from 5 to 300, more preferably from 10 to 200, more preferably from 20 to 150, and even more preferably from 40 to 120. It is particularly preferred according to the inventive process that the $YO_2$:$X_2O_3$ molar ratio of the mixture provided in step (1) is comprised in the range of from 50 to 100.

Thus, according to preferred embodiments of the present invention, the $YO_2$:$X_2O_3$ molar ratio of the mixture according to step (1) ranges from 1 to 400 or greater, preferably from 5 to 300, more preferably from 10 to 200, more preferably from 20 to 150, more preferably from 40 to 120, and even more preferably from 50 to 100.

According to particular embodiments of the present invention which are further preferred, the $YO_2$:$X_2O_3$ molar ratio of the mixture provided in step (1) is comprised in the range of from 5 to 400, preferably of from 10 to 300, more preferably of from 50 to 250, more preferably of from 70 to 200, more preferably of from 80 to 150, more preferably of from 85 to 120, and even more preferably of from 90 to 100. Alternatively, according to further embodiments of the present invention which are preferred, the $YO_2$:$X_2O_3$ molar ratio of the mixture provided in step (1) is comprised in the range of from 1 to 300, preferably from 5 to 200, more preferably from 10 to 150, more preferably from 20 to 100, more preferably from 30 to 80, more preferably from 35 to 70, more preferably from 40 to 60, and even more preferably from 45 to 55.

In embodiments of the present invention which are further preferred, the zeolitic material obtained and/or obtainable and/or the inventive material as such according to the inventive process comprises at least on alkali metal M, preferably sodium and/or potassium, and more preferably sodium. The alkali metal can be added at any conceivable stage of the inventive process, wherein preferably it is also added in step (1). More preferably, the entire quantity of the alkali metal comprised in the zeolitic material comprising $YO_2$ and optionally comprising $X_2O_3$, preferably comprising $YO_2$ and $X_2O_3$, obtained in step (2) is added in step (1) of the inventive process. In some embodiments of the inventive process, the alkali metal is partly or entirely contained in the one or more sources for $YO_2$ and/or $X_2O_3$ provided in step (1), and preferably entirely in the at least one source for $X_2O_3$.

According to the process of the present invention, the mixture provided in step (1) can contain one or more sources for hydroxide anions $OH^-$. In general any conceivable source for $OH^-$ can be used, wherein the at least one source preferably comprises a metal hydroxide, more preferably a hydroxide of an alkali metal M, more preferably sodium and/or potassium hydroxide, and even more preferably sodium hydroxide. In preferred embodiments of the inventive process, wherein the mixture comprises a silicate as a source for $YO_2$ and/or an aluminate as a source for $X_2O_3$, it is particularly preferred that the mixture does not contain a source for $OH^-$, and in particular does not contain a hydroxide, preferably a metal hydroxide, more preferably a hydroxide of an alkali metal M, more preferably sodium and/or potassium hydroxide, and even more preferably does not contain sodium hydroxide.

Furthermore, according to the inventive process there is no particular restriction as to the pH of the mixture provided in step (1) provided that a zeolitic material provided that a zeolitic material comprising $YO_2$ and optionally comprising $X_2O_3$, preferably comprising $YO_2$ and $X_2O_3$, can be crystallized in step (2). Thus, by way of example, the pH of the mixture provided in step (1) of the inventive process may range anywhere from 8 to 14. According to the present invention it is however preferred that the pH of the mixture provided in step (1) is comprised in the range of from 10 to 14, more preferably of from 11 to 14, more preferably of from 12 to 14, and even more preferably of from 13 to 14. According to some embodiments of the inventive process the pH of the mixture provided in step (1) is comprised in the range of from 13.6 to 13.8.

Therefore, according to the present invention it is preferred that the pH of the mixture provided in step (1) of the inventive process is comprised in the range of from 8 to 14, preferably from 10 to 14, more preferably from 11 to 14, more preferably from 12 to 14, more preferably from 13 to 14, and even more preferably from 13.6 to 13.8.

In step (1) according to the present invention, the mixture can be prepared by any conceivable means, wherein mixing by agitation is preferred, preferably by means of stirring.

According to the present invention, the mixture according to step (1) of the inventive process preferably further comprises one or more solvents. In this respect, any conceivable solvents may be used in any conceivable amount, provided that a zeolitic material comprising $YO_2$ and optionally comprising $X_2O_3$, preferably comprising $YO_2$ and $X_2O_3$, can be crystallized in step (2). Thus, by way of example, the one or more solvents may be chosen from water, organic solvents, and mixtures thereof, preferably from the group consisting of distilled water, alcohols, and mixtures thereof, more preferably from the group consisting of distilled water, methanol, ethanol, propanol, and mixtures thereof. According to some embodiments of the present invention, only water and preferably only distilled water is contained in the mixture according to step (1) as the solvent.

Therefore, according to preferred embodiments of the inventive process, the mixture provided in step (1) further comprises a solvent, wherein said solvent preferably comprises water, more preferably distilled water, wherein even more preferably the solvent is water, preferably distilled water.

As regards the one or more solvents which are preferably provided in the mixture according to step (1), any suitable amount thereof may be used in the mixture, provided that a zeolitic material comprising $YO_2$ and optionally comprising $X_2O_3$, preferably comprising $YO_2$ and $X_2O_3$, can be crystallized in step (2). Thus, by way of example, the $H_2O$:$YO_2$ molar ratio of the mixture provided in step (1), wherein $YO_2$ stands fro the molar amount of $YO_2$ contained in the at least one source for $YO_2$ provided in step (1), may range anywhere from 1 to 150. According to the present invention it is however preferred that the $H_2O$:$YO_2$ molar ratio of the mixture ranges from 3 to 100, preferably from 5 to 60, more preferably from 8 to 45, more preferably from 10 to 35, wherein even more preferably the molar ratio is comprised in the range of from 11 to 30. According to some embodiments, the $H_2O$:$YO_2$ molar ratio of the mixture provided in step (1) ranges from 12 to 28.

According to particular embodiments of the present invention which are further preferred, the $H_2O$:$YO_2$ molar ratio of the mixture provided in step (1) ranges from 15 to 60, preferably from 18 to 40, more preferably from 20 to 35, more preferably from 22 to 30, and even more preferably from 24 to 28. Alternatively, according to further embodiments of the present invention which are preferred, the $H_2O$:$YO_2$ molar ratio of the mixture provided in step (1) ranges from 1 to 25, preferably from 3 to 22, more preferably from 5 to 20, more preferably from 8 to 18, more preferably from 10 to 15, and even more preferably from 11 to 14.

Furthermore, as for the $H_2O$:$YO_2$ molar ratio of the mixture provided in step (1), the $H_2O$:$X_2O_3$ molar ratio of the mixture provided in step (1), wherein $X_2O_3$ stands fro the molar amount of $X_2O_3$ contained in the at least one source for $X_2O_3$ provided in step (1), may have any suitable value, provided that a zeolitic material comprising $YO_2$ and optionally comprising $X_2O_3$, preferably comprising $YO_2$ and $X_2O_3$, can be crystallized in step (2). Thus, by way of example, the $H_2O$:$X_2O_3$ molar ratio of the mixture provided in step (1) may range anywhere from 100 to 8,000. According to the present invention, the $H_2O$:$X_2O_3$ molar ratio of the mixture provided in step (1) is preferably comprised in the range of from 500 to 5,000, more preferably of from 1,000 to 3,600, and even more preferably of from 1,100 to 3,000. According to some embodiments, the $H_2O$:$X_2O_3$ molar ratio of the mixture provided in step (1) is comprised in the range of from 1,150 to 2,700.

According to particular embodiments of the present invention which are further preferred, the $H_2O$:$X_2O_3$ molar ratio of the mixture provided in step (1) ranges from 100 to 2,500, preferably from 500 to 2,000, more preferably from 1,000 to 1,700, more preferably from 1,100 to 1,500, more preferably from 1,150 to 1,400, and even more preferably from 1,200 to 1,300. Alternatively, according to further embodiments of the present invention which are preferred, the $H_2O$:$X_2O_3$ molar ratio of the mixture provided in step (1) ranges from 1,400 to 9,000, preferably from 1,600 to 7,500, more preferably from 1,800 to 6,000, more preferably from 2,000 to 4,500, more preferably from 2,200 to 3,500, more preferably from 2,400 to 3,000, and even more preferably from 2,500 to 2,700.

Thus, according to preferred embodiments of the inventive process, the $H_2O$:$YO_2$ molar ratio of the mixture provided in step (1) ranges from 1 to 150, preferably from 3 to 100, more preferably from 5 to 60, more preferably from 8 to 45, more preferably from 10 to 35, more preferably from 11 to 30, and even more preferably from 12 to 28, and/or, preferably and
wherein the $H_2O$:$X_2O_3$ molar ratio of the mixture provided in step (1) ranges from 100 to 8,000, preferably from 500 to 5,000, more preferably from 1,000 to 3,600, more preferably from 1,100 to 3,000, and even more preferably from 1,150 to 2,700.

In general, the single components for providing the mixture of step (1) of the inventive process can be added in any order, provided that a zeolitic material comprising $YO_2$ and $X_2O_3$ is crystallized from the mixture of step (1) in step (2). This may, by way of example, involve the addition of the optional solvent and the one or more ammonium compounds, followed by the addition of the one or more sources for $X_2O_3$, after which the one or more sources for $YO_2$ is then added.

In general, step (2) according to the inventive process can be conducted in any conceivable manner, provided that a zeolitic material comprising $YO_2$ and optionally comprising $X_2O_3$, preferably comprising $YO_2$ and $X_2O_3$, is crystallized from the mixture according to step (1). Thus, the mixture can be crystallized in any suitable type of vessel, wherein a means of agitation is optionally employed, preferably by rotation of the vessel and/or stirring, and more preferably by stirring the mixture. According to the inventive process, crystallization in step (2) may also be conducted under static conditions.

According to the inventive process, the mixture is preferably heated during at least a portion of the crystallization process in step (2). In general, the mixture can be heated to any conceivable temperature of crystallization, provided that a zeolitic material comprising $YO_2$ and optionally comprising $X_2O_3$, preferably comprising $YO_2$ and $X_2O_3$, is crystallized from the mixture. Thus, by way of example the mixture in step (2) may be heated to a temperature ranging anywhere from 80 to 250° C. According to the invention it is however preferred that the temperature be comprised in the range of from 100 to 200° C., more preferably from 120 to 180° C., more preferably from 130 to 170° C., and more preferably from 140 to 160° C. According to some embodiments, the crystallization process in step (2) involves heating the mixture to a temperature comprised in the range of from 145 to 155° C.

Thus, according to the inventive process it is preferred that the crystallization in step (2) involves heating of the mixture provided in step (1), preferably at a temperature ranging from 80 to 250° C., more preferably from 100 to 200° C., more preferably from 120 to 180° C., more preferably from 130 to 170° C., more preferably from 140 to 160° C., and even more preferably from 145 to 155° C.

The preferred heating in step (2) of the inventive process can be conducted in any conceivable manner suitable for the crystallization of a zeolitic material comprising $YO_2$ and optionally comprising $X_2O_3$, preferably comprising $YO_2$ and $X_2O_3$. In general, heating may be conducted at one temperature of crystallization or vary between different temperatures. Preferably, a heat ramp is used for reaching the temperature of crystallization, wherein the heating rate preferably ranges from 10 to 100° C./h, more preferably from 20 to 70° C./h, more preferably from 25 to 60° C./h, more preferably from 30 to 50° C./h, and even more preferably from 35 to 45° C./h.

In preferred embodiments of the present invention, the mixture according to step (1) is subjected in step (2) to a pressure which is elevated with regard to normal pressure. The term "normal pressure" as used in the context of the present invention relates to a pressure of 101,325 Pa in the ideal case. However, this pressure may vary within boundaries known to the person skilled in the art. By way of example, this pressure can be in the range of from 95,000 to 106,000 or of from 96,000 to 105,000 or of from 97,000 to 104,000 or of from 98,000 to 103,000 or of from 99,000 to 102,000 Pa.

In preferred embodiments of the inventive process wherein a solvent is present in the mixture according to step (1), it is furthermore preferred that heating in step (2) is conducted under solvothermal conditions, meaning that the mixture is crystallized under autogenous pressure of the solvent which is used, for example by conducting heating in an autoclave or other crystallization vessel suited for generating solvothermal conditions. In some embodiments wherein the solvent comprises water, preferably distilled water, heating in step (2) is accordingly preferably conducted under hydrothermal conditions.

Therefore, according to some embodiments of the inventive process, the heating in step (2) is conducted under solvothermal conditions, preferably under hydrothermal conditions.

The apparatus which can be used in the present invention for crystallization is not particularly restricted, provided that the desired parameters for the crystallization process can be realized, in particular with respect to the preferred embodiments requiring particular crystallization conditions. In the preferred embodiments conducted under solvothermal conditions, any type of autoclave or digestion vessel can be used, wherein a Teflon-lined apparatus is preferred.

In general, the duration of the crystallization process in step (2) of the inventive process is not particularly limited, provided that a zeolitic material comprising $YO_2$ and optionally comprising $X_2O_3$, preferably comprising $YO_2$ and $X_2O_3$, may be obtained as a crystallization product in step (2). Thus, by way of example, the duration of the crystallization process in step (2) may be comprised in the range of from 0.1 to 20 d. According to the inventive process it is however preferred that the duration of the crystallization process in step (2) ranges from 0.5 to 15 d, more preferably from 1 to 10 d, more preferably from 2 to 8 d, more preferably from 3 to 7 d, and even more preferably from 4 to 6 d. According to some embodiments of the inventive process, the duration of the crystallization process in step (2) ranges from 4.5 to 5.5 d.

Thus, according to further preferred embodiments of the inventive process wherein the crystallization in step (2) involves heating of the mixture for a period ranging from 0.1 to 20 d, preferably from 0.5 to 15 d, more preferably from 1 to 10 d, more preferably from 2 to 8 d, more preferably from 3 to 7 d, more preferably from 4 to 6 d, and even more preferably from 4.5 to 5.5 d.

According to preferred embodiments of the present invention, wherein the mixture is heated in step (2), said heating may be conducted during the entire crystallization process or during only one or more portions thereof, provided that a zeolitic material comprising $YO_2$ and $X_2O_3$ is crystallized. Preferably, heating is conducted during the entire duration of crystallization.

In general, the process of the present invention can optionally comprise further steps for the work-up and/or further physical and/or chemical transformation of the zeolitic material comprising $YO_2$ and optionally comprising $X_2O_3$, preferably comprising $YO_2$ and $X_2O_3$, is crystallized in step (2) from the mixture provided in step (1). The crystallized material can for example be subject to any sequence of isolation and/or washing procedures and/or drying procedures and/or calcination procedures and/or ion-exchange procedures, wherein the zeolitic material obtained from crystallization in step (2) is preferably subject to at least one isolation and at least one washing procedure. Within the meaning of the present invention, the term "isolation" refers to a separation of the zeolitic material, and therefore refers to a "separation" or to a step of "separating" as defined in the present invention.

Therefore, it is preferred according to the present invention that the inventive process further comprises one or more of steps of (3) isolating the zeolitic material, preferably by filtration, and/or (4) washing the zeolitic material, and/or (5) drying the zeolitic material.

In step (3) of the preferred embodiments of the inventive process, the zeolitic material may be isolated from the reaction mixture obtained in step (2) by any conceivable means, wherein by way of example any means of filtration, ultrafiltration, diafiltration, centrifugation and/or decantation methods may be employed including combinations of two or more thereof. Furthermore, the filtration methods can involve suction and/or pressure filtration steps. According to some embodiments of the present invention, the isolation of the zeolitic material in step (3) comprises one or more filtration steps, wherein more preferably the separation in step (3) is achieved by filtration.

With respect to one or more optional washing procedures in step (4), any conceivable solvent can be used. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol, such as water and methanol or water and ethanol or water and propanol or water and methanol and ethanol or water and methanol and propanol or water and ethanol and propanol or water and methanol and ethanol and propanol. Water or a mixture of water and at least one alcohol, preferably water and ethanol, is preferred, distilled water being very particularly preferred as the only washing agent.

Preferably, the separated zeolitic material is washed until the pH of the washing agent, preferably the washwater, is in the range of from 6 to 8, preferably from 6.5 to 7.5, as determined via a standard glass electrode.

Furthermore, the inventive process can optionally comprise one or more drying steps. In general, any conceivable means of drying can be used. Drying procedures preferably include heating and/or applying vacuum to the zeolitic material comprising $YO_2$ and optionally comprising $X_2O_3$, preferably comprising $YO_2$ and $X_2O_3$. In envisaged embodiments of the present invention, one or more drying steps may involve spray drying, preferably spray granulation of the zeolitic material.

In embodiments which comprise at least one drying step, the drying temperatures are preferably in the range of from 25° C. to 150° C., more preferably of from 60 to 140° C., more preferably of from 70 to 130° C. and even more preferably in the range of from 75 to 125° C. The durations of drying are preferably in the range of from 2 to 60 h, more preferably in the range of 6 to 48 hours, and even more preferably of from 12 to 24 h.

In general, the optional isolation and/or washing and/or drying procedures comprised in the inventive process can be conducted in any conceivably order and repeated one or more times.

Preferably, the inventive process comprises at least one step (3) of isolating at least a portion of the zeolitic material crystallized according to step (2), preferably by filtration thereof. According to the inventive process it is further preferred that after the at least one step of isolating, the zeolitic material is subject to at least one step of drying, wherein more preferably the zeolitic material is subject to at least one step of washing prior to the at least one drying step. In a particularly preferred embodiment, the zeolitic material crystallized according to step (2) is subject to at least one step (3) of isolating the zeolitic material from the reaction mixture obtained in step (2), followed by at least one step of washing, and then followed by at least one step of drying.

According to a further embodiment of the inventive process which is alternatively preferred, the zeolitic material crystallized in step (2) is directly subject to at least one step of drying, preferably to spray drying and/or spray granulation, without isolating, washing, or drying of the zeolitic material beforehand. Directly subjecting the reaction mixture obtained from step (2) of the inventive process to a spray drying or spray granulation stage has the advantage that isolation and drying is performed in a single stage. Consequently, according to this embodiment of the present invention, an even more preferred process is provided wherein the number of post-synthesis workup steps is minimized, as a result of which material comprising $YO_2$ and optionally comprising $X_2O_3$, preferably comprising $YO_2$ and $X_2O_3$, can be obtained from a highly simplified process.

In addition to or alternatively to one or more of the isolation, washing and/or drying procedures defined in optional steps (3), (4), and (5), the zeolitic material obtained in step (2) is preferably subject to a step (6) of calcination. In principle, calcination may be conducted at any conceivable temperature, provided that a thermally stable zeolitic material is obtained without substantial deterioration of the crystalline structure present in the zeolitic material as obtained in step (2). According to preferred embodiments, calcination of the zeolitic material is effected at a temperature comprised in the range of from 250 to 850° C., more preferably at a temperature of from 350 to 750° C., more preferably of from 450 to 650° C., more preferably of from 460 to 600° C., more preferably of from 470 to 560° C., and even more preferably of from 500 to 550° C.

According to preferred embodiments of the present invention which include a step of calcining the zeolitic material obtained according to (2), there is no particular restriction as to when the step of calcining is conducted. Thus, by way of example, the zeolitic material obtained from step (2) of the inventive process may be subject to a calcination step (6) after having isolated the zeolitic material in one or more steps (3), preferably by one or more filtration steps. It is however preferred that after having been isolated, the zeolitic material is first subject to one or more washing step (4), preferably with distilled water, prior to being subject to a calcination procedure (6), wherein even more preferably the isolated and washed zeolitic material is further subject to one or more drying procedures (5) prior to subjecting said zeolitic material to a calcination procedure (6). Alternatively, the zeolitic material crystallized in step (2) may directly be subject to one or more drying steps (4), without isolating, washing, or drying the zeolitic material beforehand, after which it is then directly subject to a calcination procedure (6). According to said alternatively preferred embodiments, direct drying of the zeolitic material obtained from step (2) is preferably achieved by spray drying and/or spray granulation, even more preferably by spray granulation.

Therefore, according to preferred embodiments, the inventive process further comprises one or more steps of
(6) calcining the zeolitic material obtained according to (2) or (3) or (4) or (5),
wherein the steps (3) and/or (4) and/or (5) and/or (6) can be conducted in any order, and
wherein at least one of said steps is preferably repeated one or more times.

The present invention furthermore relates to a synthetic zeolitic material comprising $YO_2$ and optionally comprising $X_2O_3$, preferably comprising $YO_2$ and $X_2O_3$, which is either obtained by the process according to the present invention or by any conceivable process which leads to a zeolitic material comprising $YO_2$ and optionally comprising $X_2O_3$, preferably comprising $YO_2$ and $X_2O_3$, as obtainable according to the inventive process. Within the meaning of the present invention, a material which is designated as a "synthetic" material does not signify that the designated material as such may not naturally occur in nature. In particular, a "synthetic" material only indicates that it is man-made, but by no means excludes that the material as such may occur naturally. Therefore, by way of example, the present invention also relates to a synthetic Levyne and/or to a synthetic Chabazite.

Therefore, the present invention also relates to a synthetic zeolitic material having a structure comprising $YO_2$ and optionally comprising $X_2O_3$, preferably comprising $YO_2$ and $X_2O_3$, said material being obtainable and/or obtained, preferably obtained, according to the inventive process, in particular according to preferred and particularly preferred embodiments thereof as defined in the present application.

Furthermore, the present invention also relates to a synthetic zeolitic material having a CHA framework structure comprising $YO_2$ and $X_2O_3$, wherein Y is a tetravalent element and X is a trivalent element, and wherein said synthetic zeolitic material having a CHA framework structure may optionally be obtained according to the inventive process, in particular as defined in preferred and particularly preferred embodiments of the present application. As defined in the foregoing with respect to the inventive process, $YO_2$ and $X_2O_3$ comprised in the framework structure of the zeolitic material having a CHA framework structure is contained therein as structure building elements, as opposed to non-framework elements which can be present in the pores and/or cavities formed by the CHA framework structure and typical for zeolitic materials in general.

According to the present invention, the synthetic zeolitic material having a CHA framework structure according to the present invention is characterized by its Y:X molar ratio which is comprised in the range of 1 to 10.5. In particular, Y and X refer to those tetravalent and trivalent elements respectively comprised in the framework structure of the zeolitic material. According to preferred embodiments, the Y:X molar ratio is comprised in the range of 1 to 9, wherein more preferably said molar ratio is comprised in the range of from 1 to 7, more preferably of from 1 to 6, more preferably of from 1.5 to 5, more preferably of from 1.5 to 4.5, more preferably of from 2 to 4, more preferably of from 2 to 3.75, more preferably of from 2.5 to 3.75, and even more preferably of from 3 to 3.75. According to some embodiments of the present invention, the zeolitic material having a CHA framework structure has a Y:X molar ratio which is comprised in the range of from 3.25 to 3.75.

In principle, the zeolitic material of the present invention having a CHA framework structure may comprise any conceivable tetravalent element Y, wherein Y stands for either one or several tetravalent elements. Preferred tetravalent elements according to the present invention include Si, Sn, Ti, Zr, and Ge, and combinations of two or more thereof. More preferably, Y stands for Si, Ti, or Zr, or any combination of said tetravalent elements, even more preferably for Si and/or Sn. According to the present invention, it is particularly preferred that Y stands for Si.

Furthermore, the zeolitic material having a CHA framework structure may comprise any suitable trivalent element X, wherein again X stands for either one or several trivalent elements. Preferred trivalent elements according to the present invention include Al, B, In, and Ga, and combinations thereof. More preferably, X stands for Al, B, or Ga, or any combination of said trivalent elements, even more preferably for Al and/or B. According to the present invention, it is particularly preferred that X stands for Al.

According to preferred embodiments of the present invention, the zeolitic material having a CHA framework structure further comprises $Z_2O_5$, wherein Z stands for any conceivably pentavalent element, Z standing for either one or several pentavalent elements. As defined in the foregoing with respect to the inventive process, $Z_2O_5$ which is preferably comprised in the framework structure of the zeolitic material having a CHA framework structure is contained therein as structure building element, as opposed to non-framework elements which can be present in the pores and/or cavities formed by the CHA framework structure and typical for zeolitic materials in general. Preferred pentavalent elements Z according to the present invention include P, As, Sb, Bi, V, Nb, Ta, and mixtures of two or more thereof. More preferably, Z stands for one or more elements selected from the group consisting of P, As, V, and mixtures of two or more thereof, wherein more preferably Z comprises P or As. According to some embodiments thereof, Z comprises P, wherein it is particularly preferred that Z is P.

As regards preferred embodiments of the zeolitic material having a CHA framework structure comprising Z, said particular embodiments are characterized by a Y:nX:pZ molar ratio, wherein the value for the ratio $(1+2p):(n-p)$ is comprised in the range of from 1 to 5.5. Preferably, the ratio $(1+2p):(n-p)$ in said embodiments is comprised in the range of from 1.5 to 5, more preferably in the range of from 1.5 to 4.5, more preferably of from 2 to 4, more preferably of from 2 to 3.75, more preferably of from 2.5 to 3.75, and even more preferably of from 3 to 3.75. According to some embodiments of the zeolitic material having a CHA framework structure further comprising one or more pentavalent elements Z, the value for the ratio $(1+2p):(n-p)$ is comprised in the range of from of from 3.25 to 3.75.

Therefore, the present invention further relates to a synthetic zeolitic material having a CHA framework structure, said zeolitic material being optionally obtainable and/or obtained according to the inventive process, and in particular according to preferred and particularly preferred embodiments thereof as defined in the present application, wherein the zeolitic material comprises $YO_2$ and $X_2O_3$, wherein Y is a tetravalent element and X is a trivalent element, and wherein the zeolitic material displays a Y:X molar ratio comprised in the range of from 1 to 10.5, preferably of from 1 to 9, more preferably of from 1 to 7, more preferably of from 1 to 6, more preferably of from 1.5 to 5, more preferably of from 1.5 to 4.5, more preferably of from 2 to 4, more preferably of from 2 to 3.75, more preferably of from 2.5 to 3.75, more preferably of from 3 to 3.75, and even more preferably of from 3.25 to 3.75, wherein when the zeolitic material optionally further comprises $Z_2O_5$ in addition to $YO_2$ and $X_2O_3$, wherein Z is a pentavalent element, and wherein the zeolitic material then displays a Y:nX:pZ molar ratio, the value for the ratio $(1+2p):(n-p)$ is then comprised in the range of from 1 to 5.5, preferably in the range of from 1.5 to 5, more preferably of from 1.5 to 4.5, more preferably of from 2 to 4, more preferably of from 2 to 3.75, more preferably of from 2.5 to 3.75, more preferably of from 3 to 3.75, and even more preferably of from 3.25 to 3.75.

According to the present invention, there is no particular restriction as to the type of zeolite comprised in the zeolitic material having a CHA framework structure, provided that it comprises $YO_2$ and $X_2O_3$, and that the zeolitic material displays a Y:X molar ratio comprised in the range of from 1 to 10.5, wherein according to preferred embodiments further comprising $Z_2O_5$, the material displays a Y:nX:pZ molar ratio, wherein the value for the ratio $(1+2p):(n-p)$ is comprised in the range of from 1 to 5.5. In particular, the zeolitic material having a CHA framework structure may comprise one or more particular zeolites having a CHA framework structure and displaying the aforementioned characteristics with respect to $YO_2$, $X_2O_3$, and preferably $Z_2O_5$ further comprised therein. According to preferred embodiments of the present invention, the one or more zeolites comprised in the zeolitic material having a CHA framework structure are selected from the group consisting of $(Ni(deta)_2)$-UT-6, Chabazite, |Li—Na|[Al—Si—O]-CHA, DAF-5, Dehyd. Na-Chabazite, K-Chabazite (Iran), LZ-218, Linde D, Linde R, MeAPSO-47, Phi, SAPO-34, SAPO-47, SSZ-13, SSZ-62, UiO-21, Willhendersonite, ZK-14, ZYT-6, and combinations of two or more thereof.

According to alternative embodiments of the present invention which are particularly preferred, the zeolitic material having a CHA framework structure does not contain $Z_2O_5$ as a framework element in addition to $YO_2$ and $X_2O_3$, and even more preferably does not contain a pentavalent element Z. According to said alternatively preferred embodiments, Z stands for P, wherein more preferably, Z stands for P and/or As, and more preferably for one or more pentavalent elements Z selected from the group consisting of P, As, V, and mixtures of two or more thereof, wherein even more preferably Z is selected from the group consisting of P, As, Sb, Bi, V, Nb, Ta, and mixtures of two or more thereof. According to some embodiments of the present invention, the zeolitic material having a CHA framework structure does not contain any pentavalent element Z as a structure building element in its framework.

Therefore according to alternatively preferred embodiments of the present invention, the zeolitic material having a CHA framework structure does not contain a pentavalent element Z in addition to $YO_2$ and $X_2O_3$.

There is no particular restriction according to the present invention as to the surface area which the zeolitic material having a CHA framework structure may have. Thus, by way of example, the BET surface area of the zeolitic material having a CHA framework structure as determined according to DIN 66135 may range anywhere from 200 to 700 $m^2/g$. Preferably the BET surface area determined according to DIN 66135 is comprised in the range of from 400 to 650 $m^2/g$, and even more preferably in the range of from 450 to 600 $m^2/g$. According to some embodiments of the present invention the BET surface area of the zeolitic material having a CHA framework structure is comprised in the range of from 500 to 575 $m^2/g$.

In addition to a zeolitic material having a CHA framework structure, the present invention also relates to a synthetic zeolitic material having an LEV framework structure comprising $YO_2$ and $X_2O_3$, wherein Y is a tetravalent element and X is a trivalent element, and wherein said synthetic zeolitic material having an LEV framework structure is either obtainable or directly obtained according to the inventive process, in particular as defined in preferred and particularly preferred embodiments of the present application. As defined in the foregoing with respect to the inventive process, $YO_2$ and $X_2O_3$ comprised in the framework structure of the zeolitic material having an LEV framework structure is contained therein as structure building elements, as opposed to non-framework elements which can be present in the pores and/or cavities formed by the LEV framework structure and typical for zeolitic materials in general.

According to the present invention, the synthetic zeolitic material having an LEV framework structure according to the present invention is characterized by its Y:X molar ratio which is comprised in the range of 1 to 9.25. In particular, Y and X refer to those tetravalent and trivalent elements respectively comprised in the framework structure of the zeolitic material. According to preferred embodiments, the Y:X molar ratio is comprised in the range of 2 to 9, wherein more preferably said molar ratio is comprised in the range of from 2.5 to 8.5, more preferably of from 3 to 8, more preferably of from 3.5 to 7.5, more preferably of from 4 to 7, more preferably of from 4.5 to 6.5, and even more preferably of from 5 to 6. According to some embodiments of the present invention, the zeolitic material having a CHA framework structure has a Y:X molar ratio which is comprised in the range of from 5.25 to 5.75.

In principle, the zeolitic material of the present invention having an LEV framework structure may comprise any conceivable tetravalent element Y, wherein Y stands for either one or several tetravalent elements. Preferred tetravalent elements according to the present invention include Si, Sn, Ti, Zr, and Ge, and combinations of two or more thereof. More preferably, Y stands for Si, Ti, or Zr, or any combination of said tetravalent elements, even more preferably for Si and/or Sn. According to the present invention, it is particularly preferred that Y stands for Si.

Furthermore, the zeolitic material having an LEV framework structure may comprise any suitable trivalent element X, wherein again X stands for either one or several trivalent elements. Preferred trivalent elements according to the present invention include Al, B, In, and Ga, and combinations thereof. More preferably, X stands for Al, B, or Ga, or any combination of said trivalent elements, even more preferably for Al and/or B. According to the present invention, it is particularly preferred that X stands for Al.

According to preferred embodiments of the present invention, the zeolitic material having an LEV framework structure further comprises $Z_2O_5$, wherein Z stands for any conceivably pentavalent element, Z standing for either one or several pentavalent elements. As defined in the foregoing with respect to the inventive process, $Z_2O_5$ which is preferably comprised in the framework structure of the zeolitic material having an LEV framework structure is contained therein as structure building element, as opposed to non-framework elements which can be present in the pores and/or cavities formed by the LEV framework structure and typical for zeolitic materials in general. Preferred pentavalent elements Z according to the present invention include P, As, Sb, Bi, V, Nb, Ta, and mixtures of two or more thereof. More preferably, Z stands for one or more elements selected from the group consisting of P, As, V, and mixtures of two or more thereof, wherein more preferably Z comprises P or As. According to particularly preferred embodiments thereof, Z comprises P, wherein it is particularly preferred that Z is P.

As regards preferred embodiments of the zeolitic material having an LEV framework structure comprising Z, said particular embodiments are characterized by a Y:nX:pZ molar ratio, wherein the value for the ratio $(1+2p):(n-p)$ is comprised in the range of from 1 to 20. Preferably, the ratio $(1+2p):(n-p)$ in said embodiments is comprised in the range of from 1 to 15, more preferably of from 1 to 10, more preferably of from 2 to 9, more preferably of from 2.5 to 8.5, more preferably of from 3 to 8, more preferably of from 3.5 to 7.5, more preferably of from 4 to 7, more preferably of from 4.5 to 6.5, and even more preferably of from 5 to 6. According to particularly preferred embodiments of the zeolitic material having an LEV framework structure further comprising one or more pentavalent elements Z, the value for the ratio $(1+2p):(n-p)$ is comprised in the range of from of from 5.25 to 5.75.

Therefore, the present invention further relates to a synthetic zeolitic material having an LEV framework structure, said zeolitic material being obtainable and/or obtained according to the inventive process, and in particular according to preferred and particularly preferred embodiments thereof as defined in the present application, wherein the zeolitic material comprises $YO_2$ and $X_2O_3$, wherein Y is a tetravalent element and X is a trivalent element, and wherein the zeolitic material displays a Y:X molar ratio comprised in the range of from 1 to 9.25, more preferably of from 2 to 9, more preferably of from 2.5 to 8.5, more preferably of from 3 to 8, more preferably of from 3.5 to 7.5, more preferably of from 4 to 7, more preferably of from 4.5 to 6.5, more preferably of from 5 to 6, and even more preferably of from 5.25 to 5.75,
wherein when the zeolitic material optionally further comprises $Z_2O_5$ in addition to $YO_2$ and $X_2O_3$, wherein Z is a pentavalent element, and
wherein the zeolitic material then displays a Y:nX:pZ molar ratio, the value for the ratio $(1+2p):(n-p)$ is then comprised in the range of from 1 to 20, preferably in the range of from 1 to 15, more preferably of from 1 to 10, more preferably of from 2 to 9, more preferably of from 2.5 to 8.5, more preferably of from 3 to 8, more preferably of from 3.5 to 7.5, more preferably of from 4 to 7, more preferably of from 4.5 to 6.5, more preferably of from 5 to 6, and even more preferably of from 5.25 to 5.75.

According to the present invention, there is no particular restriction as to the type of zeolite comprised in the zeolitic material having an LEV framework structure, provided that it comprises $YO_2$ and $X_2O_3$, and that the zeolitic material displays a Y:X molar ratio comprised in the range of from 1 to 9.25, wherein according to preferred embodiments further comprising $Z_2O_5$, the material displays a Y:nX:pZ molar ratio, wherein the value for the ratio $(1+2p):(n-p)$ is comprised in the range of from 1 to 20. In particular, the zeolitic material having an LEV framework structure may comprise one or more particular zeolites having an LEV framework structure and displaying the aforementioned characteristics with respect to $YO_2$, $X_2O_3$, and preferably $Z_2O_5$ further comprised therein. According to preferred embodiments of the present invention, the one or more zeolites comprised in the zeolitic material having an LEV framework structure are selected from the group consisting Levyne, LZ-132, NU-3, RUB-1, ZK-20, ZSM-45, RUB-50, and mixtures of two or more thereof, wherein it is particularly preferred according to the present invention that the zeolitic material having an LEV framework structure comprises RUB-50.

According to alternative embodiments of the present invention which are particularly preferred, the zeolitic material having an LEV framework structure does not contain $Z_2O_5$ as a framework element in addition to $YO_2$ and $X_2O_3$, and even more preferably does not contain a pentavalent element Z. According to said alternatively preferred embodiments, Z stands for P, wherein more preferably, Z stands for P and/or As, and more preferably for one or more pentavalent elements Z selected from the group consisting of P, As, V, and mixtures of two or more thereof, wherein even more preferably Z is selected from the group consisting of P, As, Sb, Bi, V, Nb, Ta, and mixtures of two or more thereof. According to particularly preferred embodiments of the present invention, the zeolitic material having an LEV framework structure does not contain any pentavalent element Z as a structure building element in its framework.

Therefore according to alternatively preferred embodiments of the present invention, the zeolitic material having an LEV framework structure does not contain a pentavalent element Z in addition to $YO_2$ and $X_2O_3$.

Furthermore, in addition to the zeolitic material having a CHA framework structure and to a zeolitic material having an LEV framework structure, the present invention also relates for a synthetic zeolitic material having a layered structure comprising $YO_2$ and optionally comprising $X_2O_3$, wherein Y is a tetravalent element, and X is a trivalent element, and wherein said synthetic zeolitic material having a layered structure may optionally be obtained according to the inventive process, in particular as defined in preferred and particularly preferred embodiments of the present application. As defined in the foregoing with respect to the inventive process, $YO_2$ and optionally $X_2O_3$ comprised in the framework structure of the zeolitic material having a layered structure is contained therein as structure building elements, as opposed to non-framework elements which can be present in the pores and/or cavities and/or between the layers of the zeolitic material having a layered structure.

According to the present invention, the synthetic zeolitic material having a layered structure has an X-ray diffraction pattern comprising at least the following reflections:

| Diffraction angle 2 Theta/° [Cu K(alpha 1)] | Intensity (%) |
|---|---|
| 5.5-5.8 | 4-16 |
| 19.29-19.59 | 7-19 |
| 20.8-21.4 | 4-16 |
| 23.87-24.17 | 3-15 |
| 28.38-28.68 | 4-21 |
| 30.6-30.9 | 2-14 |
| 35.98-36.28 | 1-10 | wherein 100% relates to the intensity of the maximum peak in the X-ray diffraction pattern. According to preferred embodiments of the present invention, the zeolitic material having a layered structure has an X-ray diffraction pattern comprising at least the following reflections:

| Diffraction angle 2 Theta/° [Cu K(alpha 1)] | Intensity (%) |
|---|---|
| 5.55-5.75 | 6-12 |
| 19.34-19.54 | 9-15 |
| 20.90-21.30 | 6-12 |
| 23.92-24.12 | 5-11 |
| 28.43-28.63 | 6-17 |
| 30.65-30.85 | 4-10 |
| 36.03-36.23 | 2-8 | wherein 100% relates to the intensity of the maximum peak in the X-ray diffraction pattern.

In principle, the zeolitic material of the present invention having a layered structure may comprise any conceivable tetravalent element Y, wherein Y stands for either one or several tetravalent elements. Preferred tetravalent elements according to the present invention include Si, Sn, Ti, Zr, and Ge, and combinations of two or more thereof. More preferably, Y stands for Si, Ti, or Zr, or any combination of said tetravalent elements, even more preferably for Si and/or Sn. According to the present invention, it is particularly preferred that Y stands for Si.

Furthermore, the zeolitic material having a layered structure may optionally comprise any suitable trivalent element X, wherein again X stands for either one or several trivalent elements. Preferred trivalent elements according to the present invention include Al, B, In, and Ga, and combinations thereof. More preferably, X stands for Al, B, or Ga, or any combination of said trivalent elements, even more preferably for Al and/or B. According to the present invention, it is particularly preferred that X stands for Al.

According to particularly preferred embodiments of the present invention wherein Y comprises Si, the zeolitic material having a layered structure is preferably a layered silicate, wherein according to further preferred embodiments comprising X, wherein X comprises Al, the zeolitic material having a layered structure is preferably an aluminosilicate. According to particularly preferred embodiments of the present invention, the zeolitic material having a layered structure is a layered silicate which does not further comprise one or more trivalent elements X as structure building elements of the layered structure.

Thus, the present invention further relates to a synthetic zeolitic material having a layered structure comprising $YO_2$ and optionally comprising $X_2O_3$, wherein Y is a tetravalent element, and X is a trivalent element, said material being optionally obtainable and/or obtained according to the inventive process, and in particular according to preferred and particularly preferred embodiments thereof as defined in the present application, wherein said material has an X-ray diffraction pattern comprising at least the following reflections:

| Diffraction angle 2 Theta/° [Cu K(alpha 1)] | Intensity (%) |
|---|---|
| 5.5-5.8 | 4-16 |
| 19.29-19.59 | 7-19 |
| 20.8-21.4 | 4-16 |
| 23.87-24.17 | 3-15 |
| 28.38-28.68 | 4-21 |
| 30.6-30.9 | 2-14 |
| 35.98-36.28 | 1-10 | wherein 100% relates to the intensity of the maximum peak in the X-ray diffraction pattern.

Furthermore, according to preferred embodiments of the zeolitic material having a layered structure, Y is preferably selected from the group consisting of Si, Sn, Ti, Zr, Ge, and mixtures of two or more thereof, wherein more preferably Y comprises Si, and wherein even more preferably Y is Si.

Finally, according to yet further preferred embodiments of the zeolitic material having a layered structure, X is preferably selected from the group consisting of Al, B, In, Ga, and mixtures of two or more thereof, wherein more preferably X comprises Al or Ga, wherein more preferably X comprises Al, and wherein even more preferably X is Al.

Depending on the specific needs of its application, the zeolitic material of the present invention can be employed as such, like in the form of a powder, a spray powder or a spray granulate obtained from above-described separation techniques, e.g. decantation, filtration, centrifugation, or spraying.

In many industrial applications, it is often desired on the part of the user not to employ the zeolitic material as powder or sprayed material, i.e. the zeolitic material obtained by the separation of the material from its mother liquor, optionally including washing and drying, and subsequent calcination, but a zeolitic material which is further processed to give moldings. Such moldings are required particularly in many industrial processes, e.g. in many processes wherein the zeolitic material of the present invention is employed as catalyst or adsorbent.

Accordingly, the present invention also relates to a molding comprising the inventive zeolitic material.

In general, the powder or sprayed material can be shaped without any other compounds, e.g. by suitable compacting, to obtain moldings of a desired geometry, e.g. tablets, cylinders, spheres, or the like.

Preferably, the powder or sprayed material is admixed with or coated by a suitable refractory binder. In general, suitable binders are all compounds which impart adhesion and/or cohesion between the zeolitic material particles to be bonded which goes beyond the physisorption which may be present without a binder. Examples of such binders are metal oxides, such as, for example, $SiO_2$, $Al_2O_3$, $TiO_2$, $ZrO_2$ or MgO or clays, or mixtures of two or more of these compounds. Naturally occurring clays which can be employed include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. In addition, the zeolitic material according to the present invention can be composited with a porous matrix material such as silica-alumina, silica-magnesia, silica-zirconia, silica-thoria, silica-beryllia and silica-titania as well as ternary compositions such as silica-alumina-thoria, silica-alumina-zirconia, silica-alumina-magnesia and silica-magnesia-zirconia.

The zeolitic material of the present invention may therefore also be provided in the form of extrudates, pellets, tablets or particles of any other suitable shape, for use as a packed bed of particulate catalyst, or as shaped pieces such as plates, saddles, tubes, or the like.

Also preferably, the powder or the sprayed material, optionally after admixing or coating by a suitable refractory binder as described above, is formed into a slurry, for example with water, which is deposited upon a suitable refractory carrier. The slurry may also comprise other compounds such as, e.g., stabilizers, defoamers, promoters, or the like. Typically, the carrier comprises a member, often referred to as a "honeycomb" carrier, comprising one or more refractory bodies having a plurality of fine, parallel gas flow passages extending therethrough. Such carriers are well known in the art and may be made of any suitable material such as cordierite or the like.

In general, the zeolitic material described above can be used as molecular sieve, adsorbent, catalyst, catalyst support or binder thereof. For example, the zeolitic material can be used as molecular sieve to dry gases or liquids; for selective molecular separation, e.g. for the separation of hydrocarbons or amides; as ion exchanger; as chemical carrier; as adsorbent, in particular as adsorbent for the separation of hydrocarbons or amides; or as a catalyst. Most preferably, the zeolitic material according to the present invention is used as a catalyst and/or as a catalyst support.

Within the meaning of the present invention, the use of a zeolitic material according to the present invention, and in particular according to preferred and particularly preferred embodiments thereof as defined in the present application, refers both to the individual zeolitic materials of the invention which are synthetic zeolitic materials comprising $YO_2$ and optionally comprising $X_2O_3$, preferably comprising $YO_2$ and $X_2O_3$, obtainable and/or obtained and preferably obtained according to the inventive process, and in particular according to preferred and particularly preferred embodiments of the inventive process as defined in the present application, as well as to the zeolitic materials having a CHA framework structure, having an LEV framework structure, and having a layered structure, respectively. In particular, the use of a zeolitic material according to the present invention preferably refers to any one or more of a synthetic zeolitic material having a CHA framework structure according to the present invention, a synthetic zeolitic material having an LEV framework structure according to the present invention, a zeolitic material having a layered structure according to the present invention, and combinations of two or more thereof. It is however particularly preferred according to the present invention that the use of a zeolitic material refers either to the zeolitic material having a CHA framework structure, having an LEV framework structure, or having a layered structure, respectively.

According to a preferred embodiment of the present invention, the zeolitic material of the invention is used in a catalytic process, preferably as a catalyst and/or catalyst support, and more preferably as a catalyst. In general, the zeolitic material of the invention can be used as a catalyst and/or catalyst support in any conceivable catalytic process, wherein processes involving the conversion of at least one organic compound is preferred, more preferably of organic compounds comprising at least one carbon-carbon and/or carbon-oxygen and/or carbon-nitrogen bond, more preferably of organic compounds comprising at least one carbon-carbon and/or carbon-oxygen bond, and even more preferably of organic compounds comprising at least one carbon-carbon bond. In particularly preferred embodiments of the present invention, the zeolitic material is used as a catalyst and/or catalyst support in a fluid catalytic cracking (FCC) process.

Furthermore, it is preferred according to the present invention, that the zeolitic material is used as a catalyst for producing light olefins from non-petroleum feedstock by conversion of oxygenates, such as lower alcohols (methanol, ethanol), ethers (dimethyl ether, methyl ethyl ether), esters (dimethyl carbonate, methyl formate) and the like to olefins, and especially in the conversion of lower alcohols to light olefins. According to particularly preferred embodiments, the zeolitic material of the present invention is used in the conversion of methanol to olefin (MTO)

According to a further embodiment of the present invention, the zeolitic material of the invention is preferably used in a catalytic process involving the conversion of at least one compound comprising at least one nitrogen-oxygen bond. Particularly preferred according to the present invention is the use of the zeolitic material comprising $YO_2$ and $X_2O_3$ as a catalyst and/or catalyst support in a selective catalytic reduction (SCR) process for the selective reduction of nitrogen oxides $NO_x$; for the oxidation of $NH_3$, in particular for the oxidation of $NH_3$ slip in diesel systems; for the decomposition of $N_2O$. The term nitrogen oxides, $NO_x$, as used in the context of the present invention designates the oxides of nitrogen, especially dinitrogen oxide ($N_2O$), nitrogen monoxide (NO), dinitrogen trioxide ($N_2O_3$), nitrogen dioxide ($NO_2$), dinitrogen tetroxide ($N_2O_4$), dinitrogen pentoxide ($N_2O_5$), nitrogen peroxide ($NO_3$). According to particularly preferred embodiments of the present invention, the zeolitic material used in a catalytic process involving the conversion of at least one compound comprising at least one nitrogen-oxygen bond comprises Cu and/or Fe, and more preferably Cu.

Therefore, the present invention also relates to a method for selectively reducing nitrogen oxides $NO_x$ by contacting a stream containing $NO_x$ with a catalyst containing the zeolitic material comprising $YO_2$ and $X_2O_3$ according to the present invention under suitable reducing conditions; to a method of oxidizing $NH_3$, in particular of oxidizing $NH_3$ slip in diesel systems, by contacting a stream containing $NH_3$ with a catalyst containing the zeolitic material comprising $YO_2$ and $X_2O_3$ according to the present invention under suitable oxidizing conditions; to a method of decomposing of $N_2O$ by contacting a stream containing $N_2O$ with a catalyst containing the zeolitic material comprising $YO_2$ and $X_2O_3$ according to the present invention under suitable decomposition conditions; to a method of controlling emissions in Advanced Emission Systems such as Homogeneous Charge Compression Ignition (HCCI) engines by contacting an emission stream with a catalyst containing the zeolitic material comprising $YO_2$ and $X_2O_3$ according to the present invention under suitable conditions; to a fluid catalytic cracking FCC process wherein the zeolitic material comprising $YO_2$ and $X_2O_3$ according to the present invention is employed as additive; to a method of converting an organic compound by contacting said compound with a catalyst containing the zeolitic material comprising $YO_2$ and $X_2O_3$ according to the present invention under suitable conversion conditions; to a "stationary source" process wherein a catalyst is employed containing the zeolitic material comprising $YO_2$ and $X_2O_3$ according to the present invention.

Therefore, the present invention also relates to a method for selectively reducing nitrogen oxides $NO_x$, wherein a gaseous stream containing nitrogen oxides $NO_x$, preferably also containing ammonia and/or urea, is contacted with the zeolitic material according to the present invention or the zeolitic material obtainable of obtained according to the present invention, preferably in the form of a molded catalyst, still more preferably as a molded catalyst wherein the zeolitic material is deposited on a suitable refractory carrier, still more preferably on a "honeycomb" carrier.

The nitrogen oxides which are reduced using a catalyst containing the zeolitic material according to the present invention or the zeolitic material obtainable of obtained according to the present invention may be obtained by any process, e.g. as a waste gas stream. Among others, waste gas streams as obtained in processes for producing adipic acid, nitric acid, hydroxylamine derivatives, caprolactame, glyoxal, methyl-glyoxal, glyoxylic acid or in processes for burning nitrogeneous materials may be mentioned.

Most preferably, the zeolitic material according to the present invention or the zeolitic material obtainable of obtained according to the present invention is used as a molded catalyst, still more preferably as a molded catalyst wherein the zeolitic material is deposited on a suitable refractory carrier, still more preferably on a "honeycomb" carrier, for the selective reduction of nitrogen oxides $NO_x$, i.e. for selective catalytic reduction of nitrogen oxides. In particular, the selective reduction of nitrogen oxides wherein the zeolitic material according to the present invention is employed as catalytically active material is carried out in the presence ammonia or urea. While ammonia is the reducing agent of choice for stationary power plants, urea is the reducing agent of choice for mobile SCR systems. Typically, the SCR system is integrated in the engine and vehicle design and, also typically, contains the following main components: SCR catalyst containing the zeolitic material according to the present invention; a urea storage tank; a urea pump; a urea dosing system; a urea injector/nozzle; and a respective control unit.

Furthermore, it is preferred according to the present invention that the zeolitic material is used as a molecular trap for organic compounds. In general, any type of organic compound may be trapped in the zeolitic material, wherein it is preferred that the compound is reversibly trapped, such that it may be later released from the zeolitic material, preferably wherein the organic compound is released—preferably without conversion thereof—by an increase in temperature and/or a decrease in pressure. Furthermore, it is preferred that the zeolitic material is used to trap organic compounds of which the dimensions allow them to penetrate the microporous system of the molecular structure. According to yet further embodiments of the present invention, it is preferred that the trapped compounds are released under at least partial conversion thereof to a chemical derivative and/or to a decomposition product thereof, preferably to a thermal decomposition product thereof.

When preparing specific catalytic compositions or compositions for different purposes, it is also conceivable to blend the zeolitic material according to the present invention comprising $YO_2$ and $X_2O_3$ with at least one other catalytically active material or a material being active with respect to the intended purpose. It is also possible to blend at least two different inventive materials which may differ in the $YO_2:X_2O_3$ ratio, preferably in the $SiO_2:Al_2O_3$ ratio, and/or in the presence or absence of one or more further metals such as one or more transition metals and/or in the specific amounts of a further metal such as a transition metal, wherein according to particularly preferred embodiments, the one or more transition metal comprises Cu and/or Fe, more preferably Cu. It is also possible to blend at least two different inventive materials with at least one other catalytically active material or a material being active with respect to the intended purpose.

Also, the catalyst may be disposed on a substrate. The substrate may be any of those materials typically used for preparing catalysts, and will usually comprise a ceramic or metal honeycomb structure. Any suitable substrate may be employed, such as a monolithic substrate of the type having fine, parallel gas flow passages extending therethrough from an inlet or an outlet face of the substrate, such that passages are open to fluid flow therethrough (referred to as honeycomb flow through substrates). The passages, which are essentially straight paths from their fluid inlet to their fluid outlet, are defined by walls on which the catalytic material is disposed as a washcoat so that the gases flowing through the passages contact the catalytic material. The flow passages of the monolithic substrate are thin-walled channels, which can be of any suitable cross-sectional shape and size such as trapezoidal, rectangular, square, sinusoidal, hexagonal, oval, circular, etc. Such structures may contain from about 60 to about 400 or more gas inlet openings (i.e., cells) per square inch (2.54 cm×2.54 cm) of cross section.

The substrate can also be a wall-flow filter substrate, where the channels are alternately blocked, allowing a gaseous stream entering the channels from one direction (inlet direction), to flow through the channel walls and exit from the channels from the other direction (outlet direction).

The catalyst composition can be coated on the flow through or wall-flow filter. If a wall flow substrate is utilized, the resulting system will be able to remove particulate matter along with gaseous pollutants. The wall-flow filter substrate can be made from materials commonly known in the art, such as cordierite, aluminum titanate or silicon carbide. It will be understood that the loading of the catalytic composition on a wall flow substrate will depend on substrate properties such as porosity and wall thickness, and typically will be lower than loading on a flow through substrate.

The ceramic substrate may be made of any suitable refractory material, e.g., cordierite, cordierite-alumina, silicon nitride, zircon mullite, spodumene, alumina-silica magnesia, zircon silicate, sillimanite, a magnesium silicate, zircon, petalite, alpha-alumina, an aluminosilicate, and the like.

The substrates useful for the catalysts of embodiments of the present invention may also be metallic in nature and be composed of one or more metals or metal alloys. The metallic substrates may be employed in various shapes such as corrugated sheet or monolithic form. Suitable metallic supports include the heat resistant metals and metal alloys such as titanium and stainless steel as well as other alloys in which iron is a substantial or major component. Such alloys may contain one or more of nickel, chromium and/or aluminum, and the total amount of these metals may advantageously comprise at least 15 wt. % of the alloy, e.g., 10-25 wt. % of chromium, 3-8 wt. % of aluminum and up to 20 wt. % of nickel. The alloys may also contain small or trace amounts of one or more other metals such as manganese, copper, vanadium, titanium, and the like. The surface or the metal substrates may be oxidized at high temperatures, e.g., 1000° C. and higher, to improve the resistance to corrosion of the alloys by forming an oxide layer on the surfaces of the substrates. Such high temperature-induced oxidation may enhance the adherence of the refractory metal oxide support and catalytically promoting metal components to the substrate.

In alternative embodiments, zeolitic material according to the present invention comprising $YO_2$ and $X_2O_3$ may be deposited on an open cell foam substrate. Such substrates are well known in the art, and are typically formed of refractory ceramic or metallic materials.

Especially preferred is the use of a catalyst containing the zeolitic material according to the present invention or the zeolitic material obtainable or obtained according to the present invention for removal of nitrogen oxides $NO_x$ from exhaust gases of internal combustion engines, in particular diesel engines, which operate at combustion conditions with air in excess of that required for stoichiometric combustion, i.e., lean.

Therefore, the present invention also relates to a method for removing nitrogen oxides $NO_x$ from exhaust gases of internal combustion engines, in particular diesel engines, which operate at combustion conditions with air in excess of that required for stoichiometric combustion, i.e., at lean conditions, wherein a catalyst containing the zeolitic material according to the present invention or the zeolitic material obtainable or obtained according to the present invention is employed as catalytically active material.

The present invention therefore relates to the use of the zeolitic material of the invention, in particular in the field of catalysis and/or in the treatment of exhaust gas, wherein said exhaust gas treatment comprises industrial and automotive exhaust gas treatment. In these and other applications, the zeolitic material of the present invention can by way of example be used as a molecular sieve, catalyst, and/or catalyst support.

In embodiments of the present invention involving the use of the zeolitic material of the invention in exhaust gas treatment, the zeolitic material is preferably used in the treatment of industrial or automotive exhaust gas, more preferably as a molecular sieve in said applications. In a particularly preferred embodiment, the zeolitic material used in exhaust gas treatment is comprised in a hydrocarbon trap.

Therefore, the present invention further relates to the use of a zeolitic material according to the present invention, and in particular according to preferred and particularly preferred embodiments thereof as defined in the present application, as a molecular sieve, as an adsorbent, for ion-exchange, as a catalyst and/or as a catalyst support, preferably as a catalyst for the selective catalytic reduction (SCR) of nitrogen oxides $NO_x$; for the oxidation of $NH_3$, in particular for the oxidation of $NH_3$ slip in diesel systems; for the decomposition of $N_2O$; as an additive in fluid catalytic cracking (FCC) processes; or as a catalyst in organic conversion reactions, preferably in the conversion of alcohols to olefins, and more preferably in methanol to olefin (MTO) catalysis.

EXAMPLES

Example 1

Preparation of a Zeolitic Material Having a CHA Framework Structure Using the N,N-dimethylpiperidinium Cation as Structure Directing Agent 153.8 g of an aqueous solution having 24.0 wt.-% of N,N-dimethylpiperidine hydroxide were weighed into a Teflon® receptacle, after which 1.4 g of $NaAlO_2$ were added and the resulting mixture stirred for 10 min. A total of 14.8 g of fumed silica (Aerosil 200) were then added to the mixture while stirring, and the resulting mixture stirred for an additional 15 min to afford a pale white translucent mixture having a pH of 13.7. The mixture was then transferred to an autoclave and crystallized at 150° C. for 120 h (5 days). After having let the reaction mixture cool to room temperature, the clear solution containing a white solid obtained as the reaction product was filtered over a glass frit, and the residue washed with 2 l of distilled water. The white solid was then dried at 120° C. for 16 h to afford 4.3 g of a white powder.

Electron Probe Micro Analysis of the crystalline product of Example 1 via Energy Dispersive X-Ray Spectroscopy (EDXS) afforded an Si:Al molar ratio of 3.5.

In FIG. 1, the X-ray diffraction (XRD) pattern of the crystalline product obtained from hydrothermal synthesis after filtration and drying is displayed. In particular, the XRD pattern is typical for a CHA-type framework structure.

2 g of the washed and dried microcrystalline product was then heated to 525° C. for 10 h thus affording 1.9 g of the calcined material. The nitrogen adsorption isotherms of the calcined material were then determined according to DIN 66134 at 77 K. The evaluation of the data offered an equivalent surface of 718.63 m$^2$/g according to the Langmuir method, and a BET surface area of 550.35 m$^2$/g.

Example 2

Preparation of a Zeolitic Material Having an LEV Framework Structure Using the N,N-dimethylpiperidinium Cation as Structure Directing Agent 154.2 g of an aqueous solution having 24.0 wt.-% of N,N-dimethylpiperidine hydroxide were weighed into a Teflon® receptacle, after which 0.9 g of NaAlO$_2$ were added and the resulting mixture stirred for 10 min. A total of 14.8 g of fumed silica (Aerosil 200) were then added to the mixture while stirring and the resulting mixture stirred for an additional 15 min to afford a pale white translucent mixture having a pH of 13.7. The mixture was then transferred to an autoclave and crystallized at 150° C. for 120 h (5 days). After having let the reaction mixture cool to room temperature, the clear solution containing a white solid obtained as the reaction product was filtered over a glass frit, and the residue washed with 2 l of distilled water. The white solid was then dried at 120° C. for 16 h to afford 4.3 g of a white powder.

Figure 2:
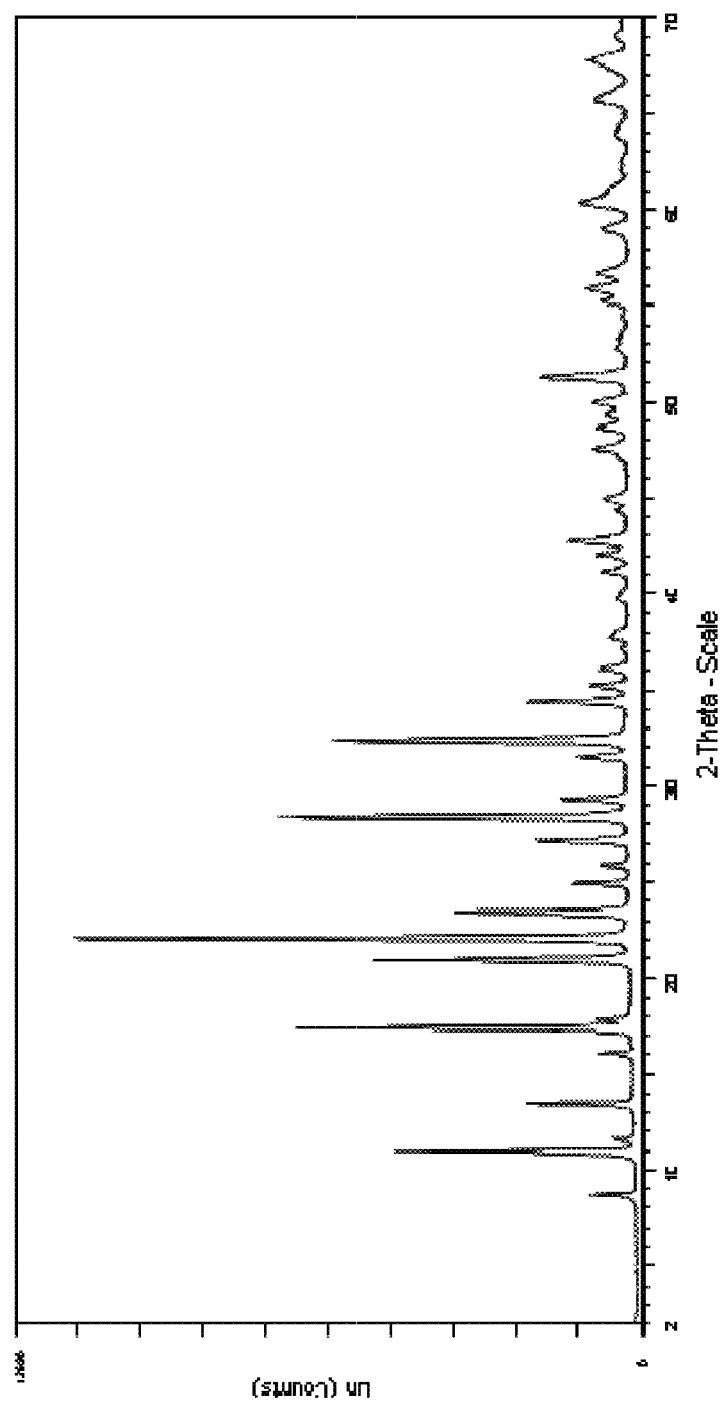

In FIG. 2, the X-ray diffraction (XRD) pattern of the crystalline product obtained from hydrothermal synthesis after filtration and drying is displayed. In particular, the XRD pattern is typical for a LEV-type framework structure.

Example 3

Preparation of a Zeolitic Material Having a Layered Structure Using the N,N-dimethylpiperidinium Cation as Structure Directing Agent 141.9 g of an aqueous solution having 24.0 wt.-% of N,N-dimethylpiperidine hydroxide were weighed into a Teflon® receptacle, after which 0.6 g of H$_3$BO$_3$ were added and the resulting mixture stirred for 10 min. A total of 27.6 g of fumed silica (Aerosil 200) were then added to the mixture while stirring and the resulting mixture stirred for an additional 15 min to afford a pale white translucent mixture. The mixture was then transferred to an autoclave and crystallized at 150° C. for 120 h (5 days). After having let the reaction mixture cool to room temperature, the clear solution containing a white solid obtained as the reaction product was filtered over a glass frit, and the residue repeatedly washed with distilled water. The white solid was then dried at 120° C. for 16 h to afford 14 g of a white powder.

Figure 3:
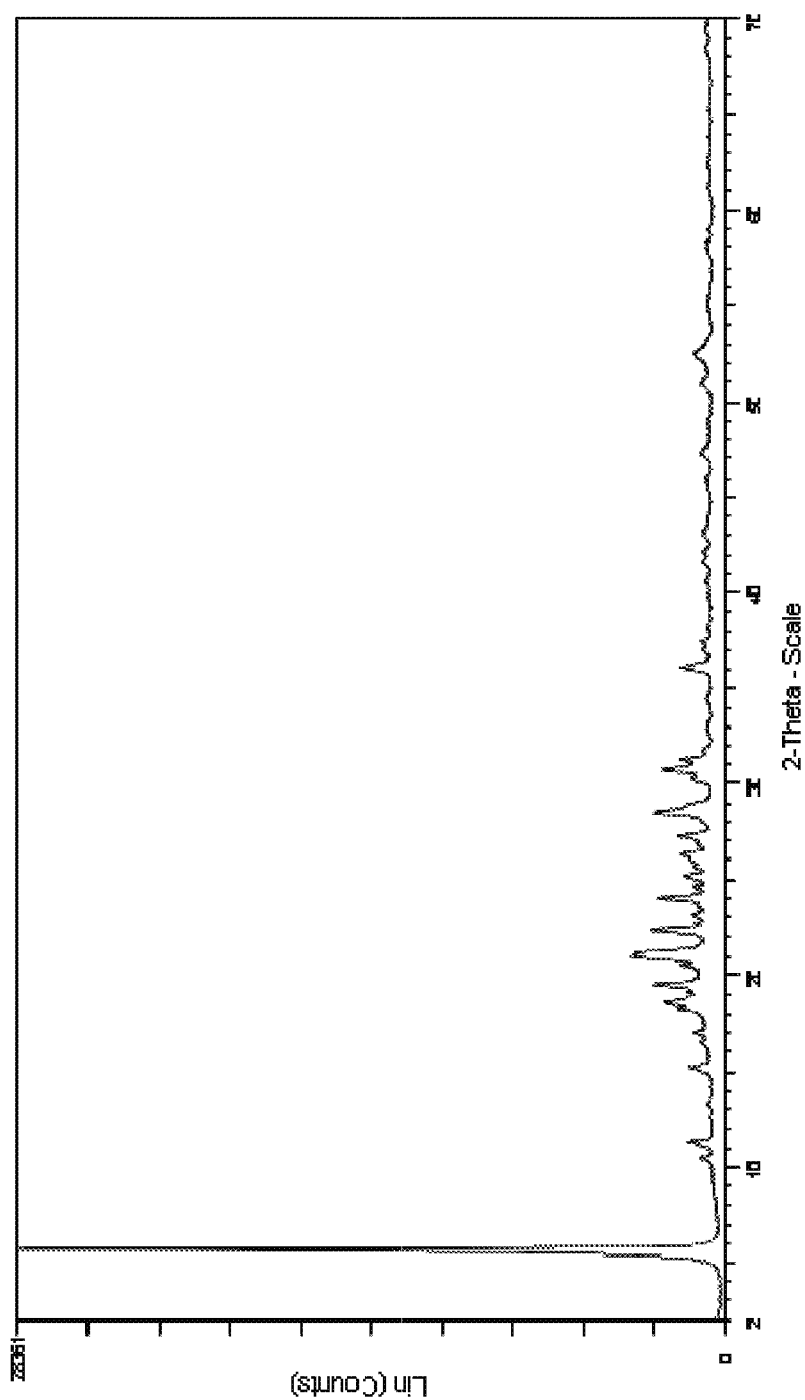

In FIG. 3, the X-ray diffraction (XRD) pattern of the crystalline product obtained from hydrothermal synthesis after filtration and drying is displayed. As may be taken from the strongest reflection at 5.645° 2 Theta, the zeolitic material has a layered structure.

TABLE 1

X-ray diffraction pattern of the layered structure of Example 3.

| Diffraction angle 2 Theta/° [Cu K(alpha 1)] | Intensity (%) |
|---|---|
| 5.645 | 100 |
| 10.425 | 2.7 |
| 11.151 | 3 |
| 11.294 | 4.6 |
| 12.548 | 1.1 |
| 13.139 | 1.6 |
| 13.26 | 1.5 |
| 15.192 | 4.1 |
| 16.457 | 2.4 |
| 16.962 | 3.5 |
| 18.273 | 5.3 |
| 18.619 | 7.4 |
| 19.437 | 8.9 |
| 20.482 | 4.8 |
| 21.006 | 11.9 |
| 21.184 | 11.4 |
| 22.398 | 9 |
| 23.086 | 3.3 |
| 24.02 | 7.9 |
| 24.622 | 3.3 |
| 25.176 | 4.2 |
| 25.675 | 3.2 |
| 26.029 | 3.7 |
| 26.31 | 4.5 |
| 26.84 | 2.5 |
| 27.261 | 5 |
| 28.024 | 1.9 |
| 28.525 | 8.5 |
| 28.858 | 4.3 |
| 30.246 | 3.4 |
| 30.746 | 7.3 |
| 31.262 | 4.6 |
| 31.771 | 1.5 |
| 32.81 | 1.1 |
| 33.193 | 0.7 |
| 34.426 | 1 |
| 36.134 | 4.5 |
| 37.043 | 1.6 |
| 37.424 | 1.7 |
| 38.232 | 0.8 |
| 40.585 | 1.1 |
| 41.66 | 1.4 |
| 42.128 | 1.5 |
| 43.188 | 1.5 |
| 43.824 | 0.8 |
| 45.601 | 0.8 |
| 45.975 | 1 |
| 47.269 | 1.8 |
| 50.913 | 1.6 |
| 52.517 | 2.7 |

Figure 4:
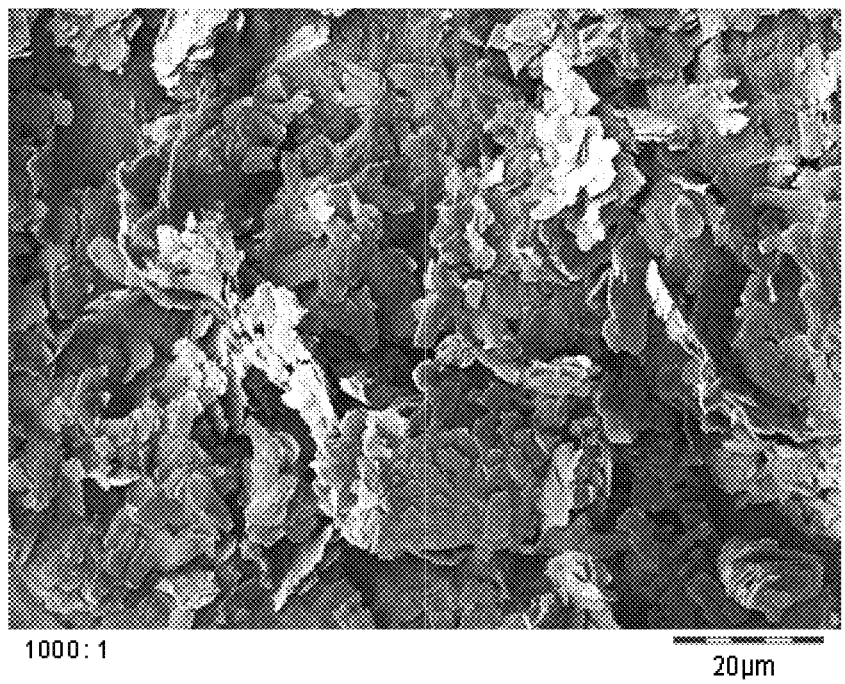
FIG. 4 shows respective scanning electron microscopy (SEM) images of the washed and dried sample obtained in Example 3. The image at the top shows a resolution of 1000:1, and in the lower right hand corner, the length of 20 micrometers as shown. The image at the bottom shows a resolution of 5000:1, and in the lower right hand corner, the length of 5 micrometers as shown.
Figure 4:
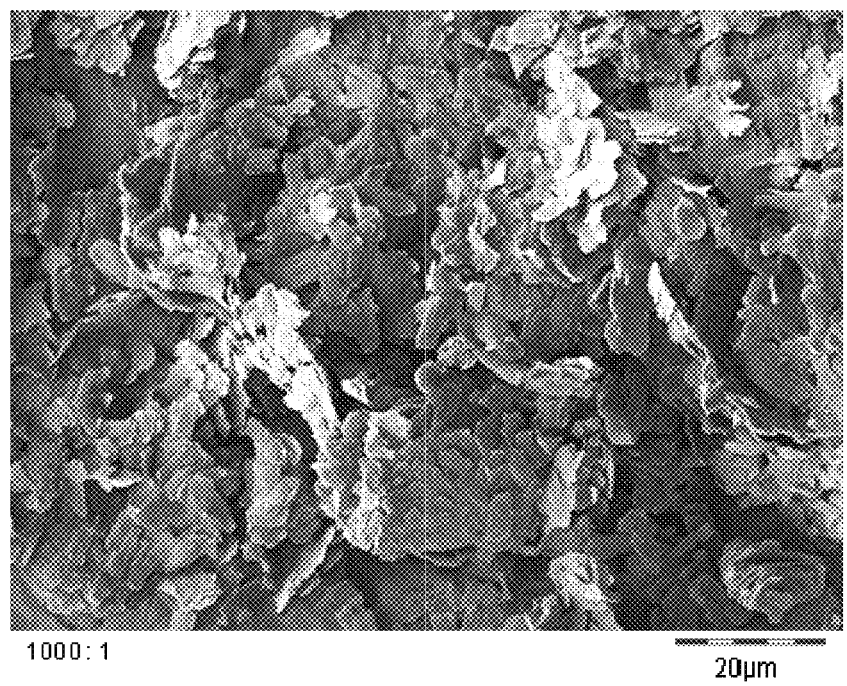

FIG. 4 displays SEM-images of the washed and dried crystalline product as obtained from hydrothermal synthesis.

What is claimed is:

1. A process for the preparation of a zeolitic material having a CHA framework structure wherein said process comprises
 (1) providing a mixture comprising
  N,N-dimethylpiperidinium hydroxide, and
  one of more sources for YO$_2$ and one or more sources for X$_2$O$_3$;
 (2) crystallizing the mixture provided in (1);
 wherein Y is a tetravalent element, and X is a trivalent element, and
 wherein the molar ratio of ammonium cation having the formula (I) to Y in the mixture provided in (1) and crystallized in (2) is equal to or greater than 0.25;
 wherein the zeolitic material comprises YO$_2$ and X$_2$O$_3$ wherein Y is a tetravalent element, and X is a trivalent element, and
 wherein the zeolitic material displays a Y:X molar ratio in the range of from 1.5 to 10.5,
 wherein the zeolitic material optionally further comprises Z$_2$O$_5$ in addition to YO$_2$ and X$_2$O$_3$, wherein Z is a pentavalent element, and wherein the zeolitic material then displays a Y:nX:pZ molar ratio, the value for the ratio (1+2p):(n−p) is in the range of from 1 to 5.5.

2. The process of claim 1, wherein Y is selected from the group consisting of Si, Sn, Ti, Zr, Ge, and mixtures of two or more thereof.

3. The process of claim 1, wherein the one or more sources for $YO_2$ comprises one or more compounds selected from the group consisting of silicas, fumed silicas, silicates, and mixtures of two or more thereof.

4. The process of claim 1, wherein X is selected from the group consisting of Al, B, In, Ga, and mixtures of two or more thereof.

5. The process of claim 1, wherein the one or more sources for $X_2O_3$ comprises one or more compounds selected from the group consisting of aluminas, aluminates, and mixtures of two or more thereof.

6. The process of claim 1, wherein the structure of the zeolitic material further comprises $Z_2O_5$ in addition to $YO_2$ and $X_2O_3$, and wherein the mixture provided in (1) further comprises one or more sources for $Z_2O_5$, wherein Z is a pentavalent element.

7. The process of claim 6, wherein Z is selected from the group consisting of P, As, Sb, Bi, V, Nb, Ta, and mixtures of two or more thereof.

8. The process of claim 1, wherein the mixture provided in step (1) further comprises a solvent.

9. The process of claim 8, wherein the solvent comprises water, and wherein the $H_2O:YO_2$ molar ratio of the mixture provided in (1) ranges from 1 to 150 and
wherein the $H_2O:X_2O_3$ molar ratio of the mixture provided in (1) ranges from 100 to 8,000.

10. The process of claim 8, wherein the solvent comprises water, and wherein the pH of the mixture provided in (1) is in the range of from 8 to 14.

11. The process of claim 1, wherein the crystallization in step (2) involves heating of the mixture.

12. The process of claim 11, wherein the heating in step (2) is conducted under solvothermal conditions.

13. The process of claim 11, wherein the crystallization in (2) involves heating of the mixture for a period ranging from 0.1 to 20 d.

14. The process of claim 1, further comprising one or more of
(3) isolating the zeolitic material, preferably by filtration, and/or
(4) washing the zeolitic material, and/or
(5) drying the zeolitic material.

15. The process of claim 14, further comprising one or more of
(6) calcining the zeolitic material obtained according to (2) or (3) or (4) or (5),
wherein the steps (3) and/or (4) and/or (5) and/or (6) can be conducted in any order.

16. A synthetic zeolitic material having a CHA framework structure, said zeolitic material being optionally obtainable and/or obtained by a process comprising
(1) providing a mixture comprising N,N-dimethylpiperidinium hydroxide
and one or more sources for $YO_2$ and one or more sources for $X_2O_3$;
(2) crystallizing the mixture provided in (1);
wherein Y is a tetravalent element, and X is a trivalent element,
wherein the molar ratio of ammonium cation having the formula (I) to Y in the mixture provided in (1) and crystallized in (2) is equal to or greater than 0.25,
wherein the zeolitic material comprises $YO_2$ and $X_2O_3$, wherein Y is a tetravalent element and X is a trivalent element, and
wherein the zeolitic material displays a Y:X molar ratio comprised in the range of from 1.5 to 10.5,
wherein when the zeolitic material optionally further comprises $Z_2O_5$ in addition to $YO_2$ and $X_2O_3$, wherein Z is a pentavalent element, and
wherein the zeolitic material then displays a Y:nX:pZ molar ratio, the value for the ratio (1+2p):(n−p) is in the range of from 1 to 5.5.

17. The synthetic zeolitic material of claim 16, wherein the material comprises one or more zeolites selected from the group consisting of (Ni(deta)$_2$)-UT-6, Chabazite, |Li—Na|[Al—Si—O]-CHA, DAF-5, Dehyd. Na-Chabazite, K-Chabazite (Iran), LZ-218, Linde D, Linde R, MeAPSO-47, Phi, SAPO-34, SAPO-47, SSZ-13, SSZ-62, UiO-21, Willhendersonite, ZK-14, ZYT-6, and combinations of two or more thereof.

18. The material of claim 16, wherein Z is selected from the group consisting of P, As, Sb, Bi, V, Nb, Ta, and mixtures of two or more thereof.

19. The material of claim 16, wherein the framework structure does not contain a pentavalent element Z in addition to $YO_2$ and $X_2O_3$.

20. The material of claim 16, wherein Y is selected from the group consisting of Si, Sn, Ti, Zr, Ge, and mixtures of two or more thereof.

21. The material of claim 16, wherein X is selected from the group consisting of Al, B, In, Ga, and mixtures of two or more thereof.

* * * * *